United States Patent
Park et al.

(10) Patent No.: US 10,919,935 B2
(45) Date of Patent: Feb. 16, 2021

(54) ANTIMICROBIAL PEPTIDE DERIVED FROM MYXINIDIN PEPTIDE AND USES THEREOF

(71) Applicant: INDUSTRY-ACADEMIC COOPERATION FOUNDATION, CHOSUN UNIVERSITY, Gwangju (KR)

(72) Inventors: Yoonkyung Park, Gwangju (KR); Hyomi Han, Gwangju (KR); Hyeonsook Cheong, Gwangju (KR)

(73) Assignee: INDUSTRY-ACADEMIC COOPERATION FOUNDATION, CHOSUN UNIVERSITY, Gwangju (KR)

(*) Notice: Subject to any disclaimer, the term of this patent is extended or adjusted under 35 U.S.C. 154(b) by 388 days.

(21) Appl. No.: 15/757,793

(22) PCT Filed: Sep. 12, 2016

(86) PCT No.: PCT/KR2016/010291
§ 371 (c)(1),
(2) Date: Mar. 6, 2018

(87) PCT Pub. No.: WO2017/048028
PCT Pub. Date: Mar. 23, 2017

(65) Prior Publication Data
US 2020/0231628 A1   Jul. 23, 2020

(30) Foreign Application Priority Data
Sep. 15, 2015 (KR) .................. 10-2015-0130339

(51) Int. Cl.
| | | |
|---|---|---|
| *C07K 7/08* | (2006.01) | |
| *A23K 20/147* | (2016.01) | |
| *A61P 17/02* | (2006.01) | |
| *A61P 31/04* | (2006.01) | |
| *A61P 29/00* | (2006.01) | |
| *A01N 37/46* | (2006.01) | |
| *A61K 8/63* | (2006.01) | |
| *A61K 47/42* | (2017.01) | |
| *A61K 38/00* | (2006.01) | |

(52) U.S. Cl.
CPC ................ *C07K 7/08* (2013.01); *A01N 37/46* (2013.01); *A23K 20/147* (2016.05); *A61K 8/63* (2013.01); *A61K 47/42* (2013.01); *A61P 17/02* (2018.01); *A61P 29/00* (2018.01); *A61P 31/04* (2018.01); *A61K 38/00* (2013.01)

(58) Field of Classification Search
CPC ......... C07K 7/08; A23K 20/147; A61P 17/02; A61P 31/04; A61P 29/00; A01N 37/46; A61K 8/63; A61K 47/42; A61K 38/00
See application file for complete search history.

(56) References Cited

FOREIGN PATENT DOCUMENTS

| KR | 10-2013-0109543 A | 10/2013 |
|---|---|---|
| KR | 10-1384577 B1 | 4/2014 |
| KR | 10-2015-0085935 A | 7/2015 |
| WO | WO2009/149554 A1 | 12/2009 |

OTHER PUBLICATIONS

Cantisani et al, Antimicrobial Agents and Chemotherapy, 2013, vol. 57, No. 11, 5665-5673 (Year: 2013).*
Cantisani et al., "Structural Insights into and Activity Analysis of the Antimicrobial Peptide Myxinidin", Antimicrobial Agents and Chemotherapy, vol. 58, No. 9, pp. 5280-5290, 2014.
Cantisani et al., "Structure-Activity Relations of Myxinidin, an Antibacterial Peptide Derived from the Epidermal Mucus of Hagfish", Antimicrobial Agents and Chemotherapy, vol. 57, No. 11, pp. 5665-5673, 2013.
Han et al., "Design and Membrane-Disruption Mechanism of Charge-Enriched AMPs Exhibiting Cell Selectivity, High-Salt Resistance, and Anti-Biofilm Properties", Amino Acids, vol. 48, No. 2, pp. 505-522, Oct. 2016.
Subramanian et al., "Myxinidin, a Novel Antimicrobial Peptide from the Epidermal Mucus of Hagfish, *Myxine glutinosa* L.", Marine Biotechnol, vol. 11, No. 6, pp. 748-757, 2009.
James A. Hill, et al., "Matrix-assisted Laser Desorption Ionization with a Magnetic Mass Spectrometer", Rapid Communications in Mass Spectrometry, vol. 5, pp. 395-399, 1991.
R.B.Merrifield, "Solid Phase Peptide Synthesis. I. The Synthesis of a Tetrapeptide", Journal of the American Chemical Society, vol. 85 (14), pp. 2149-2154, 1963.
Tomasz et al., "Multiple Antibiotic Resistance in a Bacterium with Suppressed Autolytic System", Nature, vol. 227, pp. 138-140, 1970.

* cited by examiner

*Primary Examiner* — Sudhakar Katakam
(74) *Attorney, Agent, or Firm* — The PL Law Group, PLLC

(57) ABSTRACT

A novel antimicrobial peptide is derived from myxinidin peptide. The novel antimicrobial peptides (i.e., myxinidin 2 and myxinidin 3) have low cytotoxicity for human cells while exhibiting an excellent antimicrobial activity, and exhibit an anti-inflammatory and a wound healing effect. Thus, they can be advantageously used as an effective ingredient of antibiotics, a cosmetic composition, a food additive, an animal feed additive, biopesticides, and a quasi-drug product or the like.

17 Claims, 13 Drawing Sheets
Specification includes a Sequence Listing.

SEQUENCE LISTING

```
<160> NUMBER OF SEQ ID NOS: 4

<210> SEQ ID NO 1
<211> LENGTH: 12
<212> TYPE: PRT
<213> ORGANISM: Myxine glutinosa

<400> SEQUENCE: 1

Gly Ile His Asp Ile Leu Lys Tyr Gly Lys Pro Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: artificial peptide

<400> SEQUENCE: 2

Gly Ile His His Ile Leu Lys Tyr Gly Lys Pro Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: artificial peptide

<400> SEQUENCE: 3

Lys Ile Lys Trp Ile Leu Lys Tyr Trp Lys Trp Ser
1               5                   10

<210> SEQ ID NO 4
<211> LENGTH: 12
<212> TYPE: PRT
<213> ORGANISM: Artificial Sequence
```

```
<220> FEATURE:
<223> OTHER INFORMATION: artificial peptide

<400> SEQUENCE: 4

Arg Ile Arg Trp Ile Leu Arg Tyr Trp Arg Trp Ser
1               5                   10
```

ANTIMICROBIAL PEPTIDE DERIVED FROM MYXINIDIN PEPTIDE AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/010291, filed Sep. 12, 2016, which claims priority to the benefit of Korean Patent Application No. 10-2015-0130339 filed in the Korean Intellectual Property Office on Sep. 15, 2015, the entire contents of which are incorporated herein by reference.

TECHNICAL FIELD

The present invention relates to a novel antimicrobial peptide derived from myxinidin peptide and uses thereof.

BACKGROUND ART

Bacterial infection is one of the most common and deadly causes of a human disease. However, due to abuse of antibiotics, bacterial resistance to antibiotics has been yielded unfortunately. The rate of exhibiting resistance to antibiotics by bacteria is indeed much faster than the rate of developing new antibiotics analogues. For example, various bacterial species like *Enterococcus faecalis*, *Mycobacterium tuberculosis*, and *Pseudomonas aeruginosa*, which may pose a threat to human life, have developed resistance to all antibiotics that are known until now.

Being found first in *Pneumococcus* sp. in 1970s, it provides an important key for studying the working mechanism of penicillin (Tomasz et al., Nature, 1970, 227, 138-140). Bacterial species exhibiting the tolerance show growth stall in the presence of antibiotics at common concentration, but without any death eventually. The tolerance is caused due to a lack of the activity of an autolytic bacterial enzyme like autolysin as the antibiotics inhibit an enzyme for synthesizing cell wall, and this leads to the results that, as an endogenous hydrolytic enzyme is activated by penicillin, bacterial cell death is caused, and the bacteria also suppress the enzyme activity to survive even under a treatment with antibiotics.

Having tolerance to various antibiotics by bacteria is clinically very important, because, once it becomes impossible to eradicate bacteria with tolerance, usefulness of a clinical treatment with antibiotics for infection is impaired. Furthermore, having tolerance is believed to a prerequisite requirement for developing resistance to antibiotics, and that is because there are bacterial strains which manage to survive even after a treatment with antibiotics. By acquiring new genetic elements to exhibit resistance to antibiotics, those bacterial strains keep growing even in the presence of the antibiotics. Since all bacteria exhibiting resistance are indeed known to have tolerance too, it is necessary to develop novel antibiotics which can be used for eradicating those bacteria having resistance to antibiotics.

In terms of a working mechanism, the tolerance broadly consists of two pathways. The first pathway is phenotypic tolerance which occurs during every bacteria growth with decreasing rate, and the second pathway is genetic tolerance caused by mutation which occurs in specific types of bacteria. In all of those cases, the basic phenomenon is an occurrence of down regulation of autolysin activity. This down regulation is transient in case of phenotypic tolerance against external stimulation, while it is permanent in case of genetic tolerance in which there is an occurrence of a mutation for causing a change in pathway for regulating cell lysis. The simplest genetic tolerance is based on a defect in autolysin enzyme, and due to various kinds of reasons which have not been clarified, a bacterial strain having the tolerance as caused by a defect in autolysin has not been clinically found yet, and clinical tolerance is rather achieved by regulating the activity of autolysin.

As discussed in the above, in order to deal with bacteria which exhibit resistance to antibiotics, development of new antibiotics is required, and also development of new antibiotics which work independently of the activity of autolysin is required. It is also required to provide antibiotics that are employed for an effective treatment of bacterial infection and inflammation.

Meanwhile, by synthesizing peptides or small organic molecules, bacteria may kill neighboring bacteria, and, in terms of the structure, those bacteriocins are categorized into 3 classes. First class is antibiotics, second class is nonantibiotics, and third class is those secreted by signal peptides. Animals including marine organisms also produce peptide antibiotics that are naturally produced, and those antibiotics are categorized into 3 groups. First group is cysteine-rich β-sheet peptides, second group is α-helical amphipathic molecules, and third group is proline-rich peptides. Those antibiotic peptides are known to play an important role in host defense and innate immune system. Those antibiotic peptides have various structures in accordance with their amino acid sequence, and among those structures, there is a structure forming an amphipathic α-helix with no cysteine residue like myxinidin, which is an antibiotic peptide found in epidermal mucous of a hagfish as a marine organism. Among those peptides, many studies have been made for an antibiotic activity of the amphipathic peptide originating from a marine organism, and various researches are carried out to develop antibiotics for bacteria by using the amphipathic peptide.

In Korean Patent Registration No. 1384577, "Novel antimicrobial peptide from the Yellowfin tuna, Thunnus albacores, and uses thereof" is disclosed, and in Korean Patent Application Publication No. 2015-0085935, "CMA3 analogue peptide derived from CM-MA peptide and uses thereof" is disclosed. However, the novel antimicrobial peptide derived from myxinidin peptide and uses thereof as described in the present invention have never been disclosed before.

SUMMARY

The present invention is devised under the circumstances described above. Specifically, as a result of making an effort to produce a novel synthetic peptide with enhanced antimicrobial activity from a peptide which has been previously reported to have an antimicrobial activity, the inventors of the present invention succeeded in synthesizing 3 kinds of myxinidin analogue (i.e., myxinidin 1 to myxinidin 3) by using myxinidin having amphipathic property as a template, and, by confirming that myxinidin 2 and myxinidin 3 among the synthesized peptide analogues exhibit low cytotoxicity to human erythrocyte and normal human killer cell (NHK) while exhibiting an excellent antimicrobial activity for Gram-positive bacteria, Gram-negative bacteria, and bacteria having tolerance, and are effective for anti-inflammation and wound healing, the present invention is completed accordingly.

In order to solve the problems described above, the present invention provides an antimicrobial peptide in which, in the amino acid sequence of SEQ ID NO: 1,
  i) the $1^{st}$ and the $3^{rd}$ amino acids are substituted with lysine (K) or arginine (R),
  ii) the $7^{th}$ and the $10^{th}$ amino acids are substituted with lysine (K) or arginine (R), and
  iii) the $4^{th}$, the $9^{th}$, and the $11^{th}$ amino acids are substituted with tryptophan (W).

The present invention further provides antibiotics comprising the aforementioned antimicrobial peptide as an effective ingredient.

The present invention further provides an antibiotic cosmetic composition comprising the aforementioned antimicrobial peptide as an effective ingredient.

The present invention further provides an antibiotic food additive comprising the aforementioned antimicrobial peptide as an effective ingredient.

The present invention further provides an antibiotic animal feed additive comprising the aforementioned antimicrobial peptide as an effective ingredient.

The present invention further provides antibiotic biopesticides comprising the aforementioned antimicrobial peptide as an effective ingredient.

The present invention further provides an antibiotic quasi-drug composition comprising the aforementioned antimicrobial peptide as an effective ingredient.

The present invention further provides a method for antimicrobial treatment in a subject comprising administering a pharmaceutically effective amount of the aforementioned antimicrobial peptide to a subject.

The present invention further provides an anti-inflammatory skin preparation for external use comprising the aforementioned antimicrobial peptide as an effective ingredient.

The present invention still further provides a wound-healing skin preparation for external use comprising the aforementioned antimicrobial peptide as an effective ingredient.

The present invention relates to a novel antimicrobial peptide derived from myxinidin peptide and uses thereof. Specifically, the novel antimicrobial peptides (i.e., myxinidin 2 and myxinidin 3) synthesized by using as a template a myxinidin antimicrobial peptide, which is isolated from epidermal mucous of a hagfish and has an amphipathic property, have an excellent antimicrobial activity against Gram-positive bacteria, Gram-negative bacteria, and bacteria having tolerance, and exhibit low cytotoxicity to human erythrocyte and normal human killer cell (NHK). Furthermore, by regulating cytokines, chemokines, and proteins that are related with an inflammation response to exhibit an anti-inflammatory effect and also being useful for wound healing based on an anti-microbial effect and anti-inflammatory effect in skin keratinocytes and skin tissue infected by bacterial strains having tolerance to anti-microbiotics, the novel antimicrobial peptide of the present invention can be broadly used as an effective ingredient of anti-microbial antibiotics, cosmetic composition, food additive, animal feed additive, biopesticides, quasi-drug, and the like.

BRIEF DESCRIPTION OF THE DRAWINGS

FIG. 4A: Determination of survival ratio of skin keratinocyte cells in accordance with a change in gelatin concentration; FIG. 4B: Measurement of minimum inhibitory concentration (MIC, µM) of the peptides for *Staphylococcus aureus* (*S. aureus* 3018), *Acinetobacter baumannii* (*A. baumannii* 719705), and *Pseudomonas aeruginosa* (*P. aeruginosa* 4076), in which the result is shown for different gelatin concentrations; FIG. 4C: Result of the anti-microbial disk diffusion susceptibility test carried out for *Staphylococcus aureus* (*S. aureus* 3018), *Acinetobacter baumannii* (*A. baumannii* 719705), and *Pseudomonas aeruginosa* (*P. aeruginosa* 4076), in which the result is shown for different peptide concentrations and also for the presence or absence of gelatin co-blending.

DETAILED DESCRIPTION

Figure 1A:
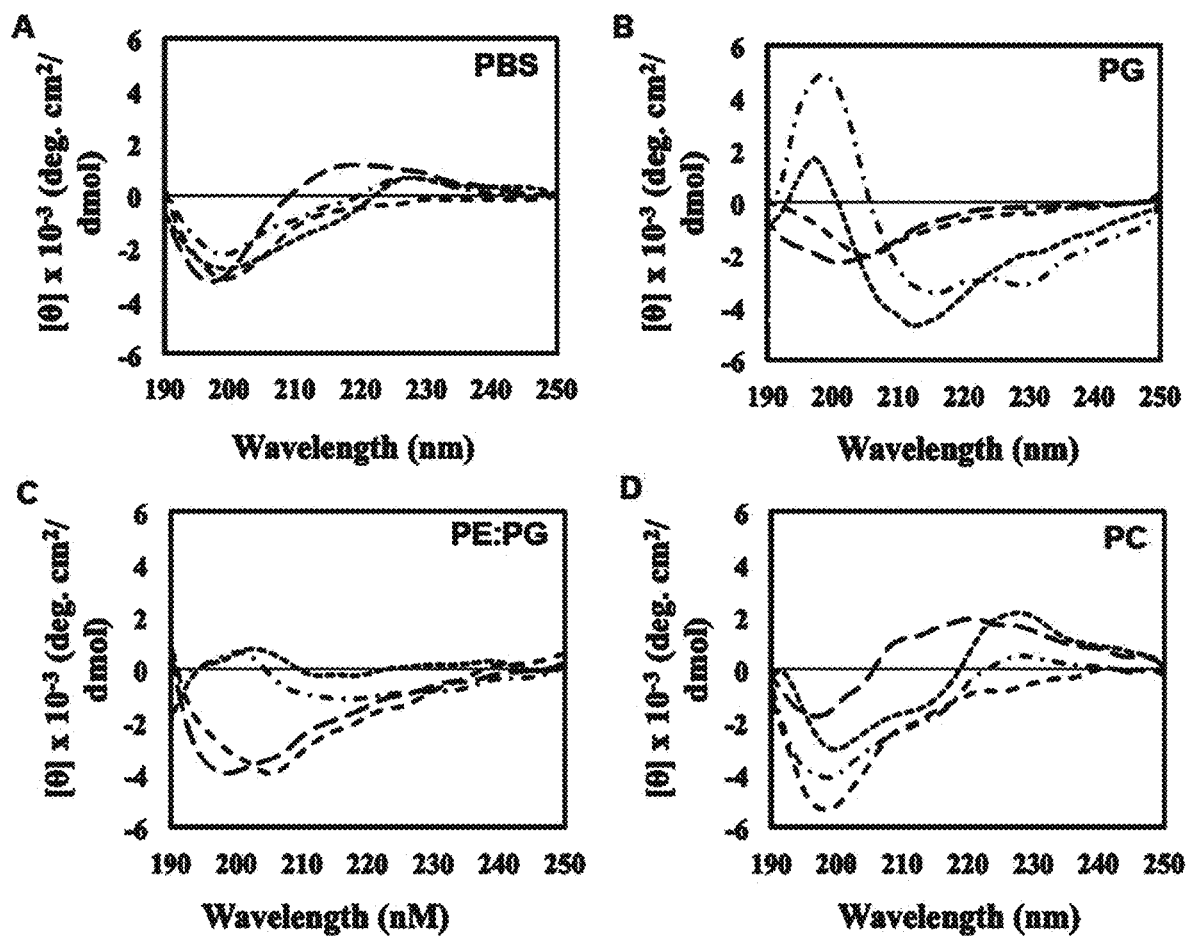
FIGS. 1A and 1B show the results of analyzing the structure of an antimicrobial peptide depending on membrane composition. --- represents myxinidin, - - represents myxinidin 1, -.- represents myxinidin 2, and . . . represents myxinidin 3. PG indicates phosphatidylglycerol; PE indicates phosphatidylethanolamine; PC indicates phosphatidylcholine; CH indicates cholesterol; and SM indicates sphingomyelin.

To achieve the purpose of the present invention, the present invention provides an antimicrobial peptide in which, in the amino acid sequence of SEQ ID NO: 1, i) the 1$^{st}$ and the 3$^{rd}$ amino acids are substituted with lysine (K) or arginine (R),
ii) the 7$^{th}$ and the 10$^{th}$ amino acids are substituted with lysine (K) or arginine (R), and
iii) the 4$^{th}$, the 9$^{th}$, and the 11$^{th}$ amino acids are substituted with tryptophan (W).

Myxinidin as a mother peptide known to have the amino acid sequence of SEQ ID NO: 1 is an antimicrobial peptide isolated from epidermal mucous of a hagfish (*Myxine glutinosa* L.), and it can be produced by a common peptide synthesis method that is known in the pertinent art. The production method is not particularly limited.

The antimicrobial peptide of the present invention needs to satisfy the requirements i), ii), and iii) described above. Specifically, in case of the requirement i), it is necessary that the 1$^{st}$ and the 3$^{rd}$ amino acids are substituted with lysine (K) or arginine (R). In this regard, not only a case in which both the 1$^{st}$ and the 3$^{rd}$ amino acids are K or R but also a case in which the 1$^{st}$ amino acid is K and the 3$^{rd}$ amino is R and a case in which the 1$^{st}$ amino acid is R and the 3$^{rd}$ amino is K may be also included. That is because K and R are both a positively charged basic amino acid so that they may have a similar activity.

Next, in case of the requirement ii), it is necessary that the 7$^{th}$ and the 10$^{th}$ amino acids are substituted with lysine (K) or arginine (R). In this regard, not only a case in which both the 7$^{th}$ and the 10$^{th}$ amino acids are K or R but also a case in which the 7$^{th}$ amino acid is K and the 10$^{th}$ amino is R and a case in which the 7$^{th}$ amino acid is R and the 10$^{th}$ amino is K may be also included. That is because K and R are both a positively charged basic amino acid so that they may have a similar activity.

Finally, in case of the requirement iii), it is necessary that the 4$^{th}$, the 9$^{th}$, and the 11$^{th}$ amino acids are substituted with tryptophan (W).

The antimicrobial peptide of the present invention preferably has the amino acid sequence of SEQ ID NO: 3 or SEQ ID NO: 4. Peptide having the amino acid sequence of SEQ ID NO: 3 is an antimicrobial peptide in which the 1$^{st}$ and the 3$^{rd}$ amino acids of myxinidin as a mother peptide are substituted with lysine (K) and the 4$^{th}$, the 9$^{th}$, and the 11$^{th}$ amino acids are substituted with tryptophan (W), and the peptide is named myxinidin 2. Peptide having the amino acid sequence of SEQ ID NO: 4 is an antimicrobial peptide in which the 1$^{st}$, the 3$^{rd}$, the 7$^{th}$, and the 10$^{th}$ amino acids of myxinidin as a mother peptide are substituted with arginine (R) and the 4$^{th}$, the 9$^{th}$, and the 11$^{th}$ amino acids are substituted with tryptophan (W), and the peptide is named myxinidin 3.

The antimicrobial peptide is most preferably a peptide consisting of the amino acid sequence of SEQ ID NO: 3 or SEQ ID NO: 4, but it is not limited thereto. According to utilization of increase/decrease of electric charge, the substitution can lower the cytotoxicity, and the substitution may be carried out to enhance or maintain the antimicrobial activity against Gram-negative bacteria and Gram-positive bacteria.

As for the method for synthesis, synthesis is preferably carried out according to a method for chemical synthesis of a peptide that is commonly employed in the pertinent art. More preferably, synthesis is carried out by a solution phase peptide synthesis, a solid-phase peptide synthesis, a fragment condensation method, or F-moc or T-BOC chemical method. Most preferably, synthesis is carried out by a solution phase peptide synthesis (Merrifield, R B., J. Am. Chem. Soc., 85, 2149, 196), but it is not limited thereto.

It is preferable that the antimicrobial peptide has an antimicrobial activity against Gram-negative bacteria, Gram-positive bacteria, or antibiotics-resistant bacteria, but it is not limited thereto.

Gram-negative bacteria are preferably all Gram-negative bacteria that are known in the pertinent art including Gram-negative bacteria of *Escherichia* sp., *Pseudomonas* sp., *Salmonella* sp., *Leptospira* sp., *Rickettsia* sp., and *Acinetobacter* sp. Gram-negative bacteria are more preferably at least one selected from a group consisting of *Escherichia* sp., *Pseudomonas* sp., *Salmonella* sp., and *Acinetobacter* sp. Gram-negative bacteria are most preferably at least one selected from a group consisting of *Escherichia coli*, *Pseudomonas aeruginosa*, *Salmonella typhimurium*, and *Acinetobacter baumannii*, but they are not limited thereto.

Gram-positive bacteria are preferably all Gram-positive bacteria that are known in the pertinent art including Gram-positive bacteria of *Staphylococcus* sp., *Listeria* sp., *Corynebacterium* sp., *Lactobacillus* sp., and *Bacillus* sp. Gram-positive bacteria are more preferably Gram-positive bacteria of *Staphylococcus* sp. or *Lactobacillus* sp. Gram-positive bacteria are most preferably *Staphylococcus aureus* or *Listeria monocytogenes*, but they are not limited thereto.

The antibiotics-resistant bacteria are preferably at least one selected from a group consisting of *Escherichia coli* (*Escherichia coli* CCARM 1229, 1238), *Pseudomonas aeruginosa* (*Pseudomonas aeruginosa* CCARM 3592, 5018, 4076), *Salmonella typhimurium* (*Salmonella typhimurium* CCARM 8009, 8013), *Staphylococcus aureus* (*Staphylococcus aureus* CCARM 3114, 3709, 3018), and *Acinetobacter baumannii* (*Acinetobacter baumannii* 719705) having antibiotics resistance, but they are not limited thereto.

Examples of the antibiotics include, although not limited thereto, aminoglycoside-based (aminoglycoside, gentamycin, neomycin, and the like), penicillin-based (ampicillin and the like), sulfonamide-based, beat-lactam based (beta-lactam, amoxicillin/clavulanic acid, and the like), chloramphenicol-based, erythromycin-based, florfenicol-based, fosfmycin-based, kanamycin-based, lincomycin-based, meticillin-based, quinolone-based, streptomycin-based, tetracycline-based, trimethoprim-based, and vancomycin-based antibiotics.

The antimicrobial peptide may exhibit low cytotoxicity for cells originating from human.

The present invention further provides antibiotics comprising the aforementioned antimicrobial peptide as an effective ingredient.

The antimicrobial peptide is preferably a peptide having the amino acid sequence of SEQ ID NO: 3 or SEQ ID NO: 4, and it is the same as described above.

Myxinidin 2 peptide or myxinidin 3 peptide, which is an analogue antimicrobial peptide derived from the myxinidin antimicrobial peptide of the present invention, exhibits low cytotoxicity for cells originating from human while showing a potent antimicrobial activity. As such, the antimicrobial peptide of the present invention can be advantageously used as an effective ingredient of antimicrobial antibiotics.

For clinical administration, the peptide of the present invention can be administered parenterally, and it can be used in the form of a common pharmaceutical preparation. Parenteral administration may mean administration via a route other than oral administration like rectal, intravenous, intraperitoneal, intramuscular, intraarterial, transdermal, nasal, inhalational, intraocular, and subcutaneous administration. When the antimicrobial peptide of the present invention is used as a pharmaceutical, one or more effective ingredient exhibiting the same or similar activity may be additionally included.

Namely, the antimicrobial peptide of the present invention can be indeed administered as various parenteral formulations, and, in case of having a preparation, production is made by using a diluent or a vehicle such as filler, bulking agent, binding agent, moisturizing agent, disintegrating agent, or surfactant that are commonly used for producing a preparation. In a preparation for parenteral administration, sterilized aqueous solution, a non-soluble agent, a suspending agent, an oil agent, a freeze-drying agent, and a suppository agent are included. As a water insoluble solvent or a suspending agent, propylene glycol, polyethylene glycol, or vegetable oil such as olive oil, and injectable ester such as ethylolate can be used. As a base for a supporitory, witepsol, macrogol, tween 61, cacao fat, laurin fat, glycerogelatin, or the like can be used.

Furthermore, the antimicrobial peptide of the present invention can be used after being admixed with various pharmaceutically acceptable carriers such as physiological saline or organic solvent. To enhance the stability or absorption property, carbohydrates such as glucose, sucrose, or dextran, anti-oxidants such as ascorbic acid or glutathione, chelating agents, low molecular weight proteins, or other stabilizers can be used as a pharmaceutical agent.

Effective dose of the antimicrobial peptide of the present invention is 0.1 to 100 mg/kg, and preferably 0.5 to 10 mg/kg. Administration can be made 1 to 3 times per day.

Total effective amount of the novel peptide of the present invention in antibiotics of the present invention can be administered to a patient as a single dose in bolus form or infusion during a relative short period of time, and it can be also administered according to a fractionated treatment protocol by which multiple dose is administered for a long period of time. With regard to the concentration described above, the effective dose is determined by considering not only the pharmaceutical administration route and number of treatment but also other various factors including age, health state, or the like of a patient. Thus, by considering them, a person having common knowledge in the pertinent art may determine suitable effective dose depending on specific use of the novel peptide of the present invention as antibiotics.

The present invention further provides an antibiotic cosmetic composition comprising the aforementioned antimicrobial peptide as an effective ingredient.

The antimicrobial peptide is preferably a peptide having the amino acid sequence of SEQ ID NO: 3 or SEQ ID NO: 4, and it is the same as described above. This peptide exhibits low cytotoxicity for cells originating from human while showing a potent antimicrobial activity. As such, the antimicrobial peptide of the present invention can be advantageously used as an effective ingredient of a cosmetic composition.

In the cosmetic composition of the present invention, ingredients commonly used for a cosmetic composition are included in addition to the antimicrobial peptide, and examples thereof include a common auxiliary agent such as an anti-oxidant, a stabilizing agent, a solubilizing agent, vitamin, a pigment, or a fragrance, and a carrier.

In the cosmetic composition of the present invention, the peptide of the present invention may be added in an amount of 0.1 to 50% by weight, and preferably 1 to 10% by weight to the cosmetic composition.

The cosmetic composition of the present invention may be produced in any formulation that is produced commonly in the pertinent art. For example, it can be produced as a formulation such as a solution, a suspension, an emulsion, paste, gel, cream, lotion, powder, a soap, a surfactant-containing cleaner, oil, powder foundation, emulsion foundation, wax foundation, or spray, but it is not limited thereto. More specifically, it can be produced as a formulation such as softening cosmetic water (skin water), nutritive cosmetic water (milk lotion), nutritive cream, massage cream, essence, eye cream, cleansing cream, cleansing foam, cleansing water, pack, spray, or powder.

When the formulation of the present invention is paste, cream, or gel, animal oil, vegetable oil, wax, paraffin, starch, tragacanth, cellulose derivatives, polyethylene glycol, silicone, bentonite, silica, talc, or zinc oxide can be used as a carrier component.

When the formulation of the present invention is powder or spray, lactose, talc, silica, aluminum hydroxide, calcium silicate, or polyamide powder can be used as a carrier component. When the formulation is spray, in particular, a propellant such as chlorofluorohydrocarbon, propane/butane, or dimethyl ether may be additionally included.

When the formulation of the present invention is a solution or an emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

When the formulation of the present invention is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth can be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamodibetaine, aliphatic alcohol, fatty acid glyceride, fatty acid diethanolamine, vegetable oil, lanolin derivatives, or ethoxylated glycerol fatty acid ester can be used as a carrier component.

The present invention further provides an antibiotic food additive comprising the aforementioned antimicrobial peptide as an effective ingredient.

The antimicrobial peptide is preferably a peptide having the amino acid sequence of SEQ ID NO: 3 or SEQ ID NO: 4, and it is the same as described above. This peptide exhibits low cytotoxicity for cells originating from human while showing a potent antimicrobial activity. As such, the antimicrobial peptide of the present invention can be advantageously used as an effective ingredient of a food additive.

When the peptide of the present invention is used as a food additive, the peptide may be directly added or used with other food components, and it can be suitably used according to a general method. Blending amount of an effective ingredient can be suitably determined depending on the purpose of use. In general, the peptide of the present invention is added in an amount of 15 parts by weight or less, and preferably 10 parts by weight or less relative to peptide raw materials. However, in case of application for a long period of time, the blending amount may be lower than the aforementioned range. As there is no problem in terms of the stability, the effective ingredient may be used in an amount that is higher than the aforementioned range.

Type of the food is not particularly limited. Examples of the food to which the additive can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all foods in general sense are included therein.

The present invention further provides an antibiotic animal feed additive comprising the aforementioned antimicrobial peptide as an effective ingredient.

The antimicrobial peptide is preferably a peptide having the amino acid sequence of SEQ ID NO: 3 or SEQ ID NO: 4, and it is the same as described above. This peptide exhibits low cytotoxicity for cells originating from human while showing a potent antimicrobial activity. As such, the antimicrobial peptide of the present invention can be advantageously used as an effective ingredient of an animal feed additive.

The animal feed composition of the present invention has an effect of replacing existing antibiotics, inhibiting growth of harmful pathogenic food bacteria to improve health state of an animal, enhancing body weight and meat quality of livestock, and enhancing milk production amount and immunity of livestock. The animal feed composition of the present invention can be produced in the form of fermented animal feed, complete animal feed, pellets, silage, or the like.

The fermented animal feed can be produced by adding various microbes or enzymes other than the peptide of the present invention to ferment organic matters, and the complete animal feed can be produced by admixing the peptide of the present invention with various kinds of common animal feed. Animal feed in pellet form can be produced by applying heat and pressure to a complete feed in a pelletizing machine, and silage can be produced by fermenting forage with the microbes of the present invention. Fermented wet animal feed can be produced by, after collecting and transporting organic matters and admixing them with a vehicle at a certain ratio for moisture control and sterilization, fermenting organic matters like food waste at a temperature suitable for fermentation for 24 hours or longer to adjust moisture content to about 70%. Fermented dry animal feed can be produced according to adjustment of the moisture content to 30% to 40% or so by providing fermented wet animal feed additionally to a drying process.

The present invention further provides an anti-septic composition comprising the aforementioned antimicrobial peptide as an effective ingredient.

The present invention further provides antibiotic biopesticides comprising the aforementioned antimicrobial peptide as an effective ingredient.

The present invention further provides an antibiotic quasi-drug composition comprising the aforementioned antimicrobial peptide as an effective ingredient.

The antimicrobial peptide is preferably a peptide having the amino acid sequence of SEQ ID NO: 3 or SEQ ID NO: 4, and it is the same as described above. This peptide exhibits low cytotoxicity for cells originating from human while showing a potent antimicrobial activity. As such, the antimicrobial peptide of the present invention can be advantageously used as an effective ingredient of antibiotic biopesticides, an anti-septic composition, or an antibiotic quasi-drug composition.

Examples of the anti-septic composition include a cosmetics preservative and a pharmaceutical preservative. The anti-septic agent for food, cosmetics preservative, and pharmaceutical preservative are an additive which is used to prevent deterioration, degradation, discoloration, and chemical change of those products, and examples thereof include a sterilizer and an anti-oxidant. Also included are functional antibiotics having an activity of inhibiting growth or sterilizing degrading bacteria in food product and pharmaceutical product according to suppression of proliferation of microbes like bacteria, fungi, and yeast. As an ideal condition required for such anti-septic composition, the composition should not have any toxicity and should exhibit the effect even with a trace amount.

When the composition of the present invention is used as a quasi-drug additive, the antimicrobial peptide may be directly added or used with other quasi-drug or quasi-drug components, and it can be suitably used according to a general method. Blending amount of an effective ingredient can be suitably determined depending on the purpose of use.

The quasi-drug composition of the present invention is preferably a sterilizing cleanser, a shower foam, a mouth wash, a water tissue, a liquid soap, a hand wash, a humidifier filler, a mask, an ointment, a patch, or a filter filler, although it is not limited thereto.

The present invention further provides a method for antimicrobial treatment in a subject comprising administering a pharmaceutically effective amount of the aforementioned antimicrobial peptide to a subject. The subject may be a mammal excluding human, but it is not limited thereto.

Since the peptide of the present invention has not only the antimicrobial activity but also a property of anti-inflammation and promoting wound healing, it can be advantageously used as an effective ingredient of a pharmaceutical composition, a cosmetic material, or a skin preparation composition for external use or the like that are used for antimicrobial treatment, anti-inflammation treatment, or wound healing.

The present invention further provides an anti-inflammatory skin preparation for external use comprising the aforementioned antimicrobial peptide as an effective ingredient.

The present invention still further provides a wound-healing skin preparation for external use comprising the aforementioned antimicrobial peptide as an effective ingredient.

The anti-inflammatory and wound healing effect of the antimicrobial peptide of the present invention is characterized by phosphorylation/activity regulation of STAT3, SAPK/JNK, P38, and EGFR in inflammation signaling pathway induced by bacteria having tolerance to antibiotics and suppressed production of cytokine and chemokine. It is also characterized by increased expression amount of epidermal growth factor receptor, which is a receptor for inducing cell proliferation, differentiation, and growth for wound healing.

According to one embodiment of the present invention, the anti-inflammation effect of the antimicrobial peptide of the present invention was confirmed by reduced phosphorylation of STAT3, SAPK/JNK, and P38, which are the proteins involved with an inflammatory response in skin keratinocyte cells infected with bacteria having tolerance to antibiotics. Furthermore, as a result of determining the expression amount of IL-6 and TNF-α as a cytokine involved with an inflammatory response and IL-8 as a chemokine, it was found that the expression amount which has been increased by infection with bacteria having tolerance to antibiotics is lowered by a treatment with the antibiotic peptide.

The inventors of the present invention also observed cell migration under a microscope to see whether or not the antimicrobial peptide exhibits any effect on wound healing after inflammation. As a result, it was confirmed that, while the cells infected with bacteria having tolerance to antibiotics did not show any cell death or migration, the antimicrobial activity and anti-inflammation effect are exhibited by the peptide in the cells infected with antimicrobial peptide, showing active cell migration to yield wound healing (see, FIGS. 7A and 7B).

The inventors of the present invention also determined specifically the effect of the antimicrobial peptide on skin wound of an infected mouse. As a result, the infected wound which has been treated with the antimicrobial peptide showed a rapid progress of epidermalization to have skin regeneration like non-infected wound as a control, and the wound healing was achieved within the same time frame as the control. On the other hand, the wound infected with bacteria having tolerance showed an increased amount of exudate and no epidermalization, indicating absence of any healing (see FIGS. 8A to 8C).

The peptide of the present invention can be parenterally administered, and it can be used in general pharmaceutical preparation form.

Namely, the peptide of the present invention can be indeed administered as various parenteral formulations, and, in case of having a preparation, production is made by using a diluent or a vehicle such as filler, bulking agent, binding agent, moisturizing agent, disintegrating agent, or surfactant that are commonly used for producing a preparation. As a moisturizing agent, gelatin can be preferably used.

According to one embodiment of the present invention, to see whether or not the antimicrobial activity is maintained when the antimicrobial peptide of the present invention is admixed with gelatin, which is used as a wound moisturizing agent, the inventors of the present invention conducted an anti-microbial disk diffusion susceptibility test. As a result, it was confirmed that the antimicrobial peptide exhibits the function while maintaining the antimicrobial activity (see FIGS. 4A to 4C).

The skin preparation composition for external use according to the present invention can be produced in the form of a pharmaceutical composition containing the peptide of the present invention in an effective amount, and one or more non-toxic and pharmaceutically acceptable carrier, auxiliary agent, diluent solution, or other component that are commonly used in the pertinent art can be included. Furthermore, the skin preparation composition for external use according to the present invention can be formulated by a known method by using a pharmaceutically acceptable carrier and vehicle.

Furthermore, the skin preparation composition for external use according to the present invention can be formulated in the form of a solution, a suspension, or an emulsion in oil or aqueous medium, or in the form of dry powder which is used after being dissolved in sterile water from which heat-generating materials are removed. A water-in-oil type emulsion is an emulsion in which vegetable oil like olive oil or mineral oil like liquid paraffin is used as an oil phase, and natural phospholipids such as soy bean lecithin, or a compound obtained by condensation of those derived from ester of hexitol anhydride like sorbitan monooleate or fatty acid, or those derived from partial ester of hexitol anhydride like polyoxyethylene sorbitol monooleate or fatty acid, with ethylene oxide is used as an emulsifying agent to emulsify the active ingredients.

When the skin preparation composition for external use according to the present invention is formulated as cosmetics, the formulation type is not particularly limited, and examples thereof include a softening cosmetic water, an astringent, a nutritive cosmetic water, an eye cream, a nutritive cream, a massage cream, a cleansing cream, a cleansing form, a cleansing water, a powder, an essence, and a pack.

Hereinbelow, the present invention is explained in greater detail in view of the Examples. However, it is evident that the following Examples are given only for exemplification of the present invention and by no means the present invention is limited to the following Examples.

EXAMPLES

Example 1: Synthesis, Isolation, and Purification of Peptide

According to the solution phase peptide synthesis by Merrifield (Merrifield, R B., J. Am. Chem. Soc., 85:2149-2154, 1963), the inventors of the present invention substituted the $4^{th}$ amino acid residue of the peptide having the amino acid sequence, which is described as myxinidin as a mother peptide, with histidine. The $1^{st}$ and the $3^{rd}$ residues were substituted with lysine and the $4^{th}$, the $9^{th}$, and the $11^{th}$ residues were substituted with tryptophan. Furthermore, the antimicrobial peptide having the amino acid sequence described as myxinidin was synthesized by substitution of the $1^{st}$, the $3^{rd}$ the $7^{th}$, and the $10^{th}$ residues with arginine and substitution of the $4^{th}$, the $9^{th}$, and the $11^{th}$ amino acid residues with tryptophan (Table 1).

Specifically, as for the peptide in which the peptide designed in the present invention has a carboxy terminal in $NH_2$ form, a rink amide MBHA-resin was used as a starting material, and as for the peptide having a carboxy terminal in OH form, a Fmoc (9-fluorenylmethoxycarbonyl)-amino acid-Wang resin was used as a starting material.

Peptide chain extension based on Fmoc-amino acid coupling was carried out by DCC (N-hydroxybenzotrizole (HOBt)-dicyclo-hexycarbodiimide) method. After coupling Fmoc-amino acid at the terminal amino acid of each peptide, the Fmoc group is removed by using NMP (20% piperidine/N-methyl pyrolidone) solution. Then, after washing several times with NMP and DCM (dichloromethane), drying with nitrogen gas was carried out. Then, a solution in which TFA (trifluoroacetic acid), phenol, thioanisole, $H_2O$, and triisopropylsilane are mixed at ratio of 85:5:5:2.5:2.5 (v/v) was added thereto followed by reaction for 2 to 3 hours to remove the protective group and separate the peptide from resin. Then, the peptide was allowed to precipitate in diethyl ether. The crude peptide obtained by the above method was purified by using a purification type reverse phase (RP)-HPLC column (Delta Pak, $C_{18}$ 300 Å, 15, 19.0 mm×30 m, Waters, USA) based on acetonitrile gradient containing 0.05% TFA. The synthesized peptide was hydrolyzed with 6 N HCl at 110° C. Then, the resulting residues were concentrated under reduced pressure and dissolved in 0.02N HCl. The amino acid composition was measured by using an amino acid analyzer (Hitachi 8500 A). To determine the purity and molecular weight of the peptide, MALDI mass analysis (Hill et. al., Rapid Commun. Mass Spectrometry, 5:395, 1991) was carried out.

As a result, as shown in the following Table 1, the peptide represented by the amino acid described with SEQ ID NO: 1 to SEQ ID NO: 4 was synthesized with purity of 95% or higher, and the molecular weight was found to be the same as the expected molecular weight (Table 1).

TABLE 1

Sequence, molecular weight, and retention time of the peptides synthesized in the present invention

| Peptide name | Amino acid sequence | Sequence ID NO. | Molecular weight | Retention time |
|---|---|---|---|---|
| Myxinidin | GIHDILKYGKPS-NH$_2$ | 1 | 1325.9 | 11.6 |
| Myxinidin 1 | GIHHILKYGKPS-NH$_2$ | 2 | 1347.9 | 7.3 |
| Myxinidin 2 | KIKWILKYWKWS-NH$_2$ | 3 | 1677.2 | 18.6 |
| Myxinidin 3 | RIRWILRYWRWS-NH$_2$ | 4 | 1789.2 | 19.3 |

| | Amino acid NO. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Myxinidin | G | I | H | D | I | L | K | Y | G | K | P | S |
| Myxinidin 2 | K | — | K | W | — | — | — | — | W | — | W | — |
| Myxinidin 3 | R | — | R | W | — | — | R | — | W | R | W | — |

—: No amino acid substitution.
Bold letter: Substituted amino acid.

Example 2: Measurement of Antimicrobial Activity

To compare the antimicrobial activity of the peptide produced by the method of Example 1, the inventors of the present invention measured the growth minimum inhibitory concentration (MIC), which is minimum concentration of the peptide showing no dissociation of bacterial cells.

Specifically, the bacterial strain described in the following Table 2 was purchased and cultured in each medium to a mid-log phase. Then, after dilution to bacterial cell concentration of 2×10$^5$ cells/100 μl, the cells were inoculated to a microtiter plate (NUNC, USA). Thereafter, myxinidin 1, myxinidin 2, or myxinidin 3 peptides which have been synthesized in Example 1 above was diluted, 1/2 times for each, with BSA (bovine serum albumin) solution in a 96-well plate. After adding the cells to a plate, the cells were cultured for 12 hours at 37° C. By using a microtiter plate reader (Merck Elisa reader, Germany), the absorbance was measured at a wavelength of 600 nm to determine the MIC value of each bacterial strain. As a control group, myxinidin as a mother peptide was subjected to the same processes as above and the MIC value of each bacterial strain was obtained.

TABLE 2

Bacterial strains used in the present invention and sources of bacterial strains

| Category | Name of bacterial strain | Source | Accession number |
|---|---|---|---|
| Gram-negative bacteria | Escherichia coli | American Type Culture Collection | ATCC 25922 |
| | Pseudomonas aeruginosa | American Type Culture Collection | ATCC 27853 |
| | Salmonella typhimurium | Korean Collection for Type Cultures | KCTC 1926 |
| Gram-positive bacteria | Staphylococcus aureus | American Type Culture Collection | ATCC 25923 |
| | Listeria monocytogenes | Korean Collection for Type Cultures | KCTC 3710 |
| Bacteria having tolerance | Escherichia coli | Culture Collection of Antimicrobial Resistant Microbes | CCARM 1229 |
| | Escherichia coli | Culture Collection of Antimicrobial Resistant Microbes | CCARM 1238 |
| | Salmonella typhimurium | Culture Collection of Antimicrobial Resistant Microbes | CCARM 8009 |
| | Salmonella typhimurium | Culture Collection of Antimicrobial Resistant Microbes | CCARM 8013 |
| | Pseudomonas aeruginosa | Isolated strain 3592 | |
| | Pseudomonas aeruginosa | Isolated strain 5018 | |
| | Staphylococcus aureus | Culture Collection of Antimicrobial Resistant Microbes | CCARM 3114 |
| | Staphylococcus aureus | Culture Collection of Antimicrobial Resistant Microbes | CCARM 3709 |

As a result, as it is shown in the following Table 3, myxinidin 2 and myxinidin 3 peptides were confirmed to exhibit more excellent antimicrobial activity for all of Gram-negative bacteria, Gram-positive bacteria, and bacterial having tolerance compared to the control group myxinidin (Table 3).

TABLE 3

Antimicrobial activity of antimicrobial peptide against Gram-negative bacteria, Gram-positive bacteria, and bacteria having tolerance

| | Minimum growth inhibitory concentration (μM) | | | | | | | | | | | | |
|---|---|---|---|---|---|---|---|---|---|---|---|---|---|
| | Gram-negative bacteria | | | Gram-positive bacteria | | Bacteria having tolerance | | | | | | | |
| | | | | | | *Escherichia coli* | | *P. aeruginosa* | | *S. typhimurium* | | *S. aureus* | |
| Peptide | *Escherichia coli* | *P. aeruginosa* | *S. typhimurium* | *S. aureus* | *L. monocytogenes* | 1229 | 1238 | 3592 | 5018 | 8009 | 8013 | 3114 | 3709 |
| Myxinidin | >32 | >32 | >32 | >32 | >32 | >32 | >32 | >32 | >32 | >32 | >32 | >32 | >32 |
| Myxinidin 1 | >32 | >32 | >32 | >32 | >32 | >32 | >32 | >32 | >32 | >32 | >32 | >32 | >32 |
| Myxinidin 2 | 1 | 4 | 2 | 0.25 | 4 | 2 | 4 | 8 | 4 | 8 | 16 | 32 | 2 |
| Myxinidin 3 | 0.5 | 2 | 1 | 0.25 | 1 | 1 | 2 | 8 | 8 | 4 | 4 | 8 | 2 |

Example 3: Measurement of Antimicrobial Activity at Salt Concentration

To compare the antimicrobial activity of the peptide produced by the method of Example 1, the inventors of the present invention measured the minimum growth inhibitory concentration (MIC), which is minimum concentration of the peptide showing no dissociation of bacterial cells, at salt concentration.

Specifically, the bacterial strain described in the above Table 2 was cultured in each medium to a mid-log phase. Then, after dilution to bacterial cell concentration of 2×10⁵ cells/100 μl, the cells were inoculated to a microtiter plate (NUNC, USA). Thereafter, myxinidin 1, myxinidin 2, or myxinidin 3 peptides which have been synthesized in Example 1 above was diluted, 1/2 times for each, with BSA+150 mM sodium chloride (NaCl) solution, physiological saline (PBS) solution, or 10 mM sodium phosphate (SP) solution in a 96-well plate. After adding the cells to a plate, the cells were cultured for 12 hours at 37° C. By using a microtiter plate reader (Merck Elisa reader, Germany), the absorbance was measured at a wavelength of 600 nm to determine the MIC value of each bacterial strain. As a control group, myxinidin as a mother peptide was subjected to the same processes as above and the MIC value of each bacterial strain was obtained.

As a result, as it is shown in the following Table 4, myxinidin 2 and myxinidin 3 peptides were confirmed to exhibit a potent antimicrobial activity for all of Gram-negative bacteria, Gram-positive bacteria, and bacterial having tolerance compared to the control group myxinidin (Table 4).

TABLE 4

Antimicrobial activity of antimicrobial peptide against Gram-negative bacteria, Gram-positive bacteria, and bacteria having tolerance according to salt concentration

| | | Peptide | | | | | | | | | | | |
|---|---|---|---|---|---|---|---|---|---|---|---|---|---|
| | | Myxinidin | | | Myxinidin 1 | | | Myxinidin 2 | | | Myxinidin 3 | | |
| | Bacterial strain | NaCl | SP | PBS | NaCl | SP | PBS | NaCl | SP | PBS | NaCl | SP | PBS |
| Gram-negative bacteria | *Escherichia coli* | >32 | >32 | >32 | >32 | >32 | >32 | 8 | 2 | 4 | 8 | 2 | 2 |
| | *P. aeruginosa* | >32 | >32 | >32 | >32 | >32 | >32 | 8 | 8 | 4 | 4 | 4 | 4 |
| | *S. typhimurium* | >32 | >32 | >32 | >32 | >32 | >32 | 2 | 2 | 4 | 2 | 2 | 2 |
| Gram-positive bacteria | *S. aureus* | >32 | >32 | >32 | >32 | >32 | >32 | 0.25 | 1 | 1 | 0.25 | 1 | 1 |
| | *L. monocytogenes* | >32 | >32 | >32 | >32 | >32 | >32 | 4 | 8 | 8 | 2 | 4 | 4 |
| Bacteria having tolerance | *Escherichia coli* 1229 | >32 | >32 | >32 | >32 | >32 | >32 | 8 | 2 | 2 | 2 | 2 | 2 |
| | *Escherichia coli* 1238 | >32 | >32 | >32 | >32 | >32 | >32 | 8 | 4 | 2 | 8 | 2 | 4 |
| | *P. aeruginosa* 3592 | >32 | >32 | >32 | >32 | >32 | >32 | 16 | 8 | 8 | 8 | 4 | 4 |
| | *P. aeruginosa* 5018 | >32 | >32 | >32 | >32 | >32 | >32 | 16 | 2 | 4 | 8 | 2 | 4 |
| | *S. typhimurium* 8009 | >32 | >32 | >32 | >32 | >32 | >32 | 8 | 4 | 4 | 4 | 2 | 4 |
| | *S. typhimurium* 8013 | >32 | >32 | >32 | >32 | >32 | >32 | 32 | 4 | 8 | 8 | 2 | 4 |
| | *S. aureus* 3114 | >32 | >32 | >32 | >32 | >32 | >32 | >32 | 8 | 16 | 16 | 4 | 4 |
| | *S. aureus* 3709 | >32 | >32 | >32 | >32 | >32 | >32 | 8 | 4 | 8 | 4 | 4 | 4 |

Example 4 Measurement of Anti-Biofilm Activity

To compare the antimicrobial activity of the peptide produced by the method of Example 1, the inventors of the present invention measured the biofilm inhibitory concentration value of the peptide showing no dissociation of bacterial cells.

Specifically, the Gram-negative bacteria and Gram-positive bacteria among the bacterial strains described in the above Table 2 were cultured in each medium to a mid-log phase. Then, after dilution to bacterial cell concentration of 5×10⁵ cells/100 μl, the cells were inoculated to a microtiter plate (NUNC, USA). Thereafter, myxinidin 1, myxinidin 2, or myxinidin 3 peptides which have been synthesized in Example 1 above was diluted, 1/10 times for each, with physiological saline (PBS) solution in a 96-well plate. After adding the cells to a plate, the cells were cultured for 12 hours at 37° C. After removing the supernatant, the cells were fixed with 100% methanol and reacted for 2 hours with Crystal violet staining solution followed by rinsing for 3 times. Then, after dissolving in 95% ethanol, the absorbance was measured at a wavelength of 595 nm by using a microtiter plate reader (Merck Elisa reader, Germany) to determine the biofilm inhibitory concentration value of each bacterial strain. As a control group, myxinidin as a mother peptide was subjected to the same processes as above and the biofilm inhibitory concentration value of each bacterial strain was obtained.

As a result, as it is shown in the following Table 5, 32 µM and 16 µM myxinidin 2 and myxinidin 3 peptides were particularly confirmed to exhibit a potent anti-biofilm activity in all bacterial strains compared to the control group myxinidin. It was also confirmed that, as the concentration increases from 2 µM, myxinidin 3 peptide inhibited the anti-biofilm activity in all bacterial strains.

TABLE 5

Anti-biofilm activity of antimicrobial peptide against Gram-negative bacteria and Gram-positive bacteria

| | | Biofilm forming ability % (concentration of each peptide, µM) | | | | | | | |
|---|---|---|---|---|---|---|---|---|---|
| | Peptide | 32 | 16 | 8 | 4 | 2 | 1 | 0.5 | 0.25 |
| P. aeruginosa | Myxinidin | 88 | 88 | 88 | 89 | 91 | 91 | 100 | 100 |
| | Myxinidin 1 | 88 | 89 | 92 | 92 | 93 | 94 | 100 | 100 |
| | Myxinidin 2 | 5 | 5 | 13 | 29 | 83 | 95 | 98 | 100 |
| | Myxinidin 3 | 7 | 7 | 7 | 8 | 64 | 97 | 97 | 100 |
| S. aureus | Myxinidin | 73 | 73 | 74 | 80 | 80 | 86 | 93 | 100 |
| | Myxinidin 1 | 75 | 79 | 83 | 83 | 86 | 87 | 88 | 98 |
| | Myxinidin 2 | 15 | 24 | 89 | 93 | 97 | 97 | 97 | 100 |
| | Myxinidin 3 | 14 | 16 | 17 | 28 | 71 | 84 | 84 | 85 |
| L. monocytogenes | Myxinidin | 95 | 99 | 100 | 100 | 100 | 100 | 100 | 100 |
| | Myxinidin 1 | 93 | 97 | 98 | 99 | 100 | 100 | 100 | 100 |
| | Myxinidin 2 | 33 | 45 | 93 | 99 | 100 | 100 | 100 | 100 |
| | Myxinidin 3 | 16 | 18 | 21 | 22 | 83 | 87 | 87 | 94 |

Example 5: Measurement of Hemolytic Activity

To compare the cytotoxicity among the peptides that are produced by the method of Example 1, erythrocyte hemolytic activity of the synthesized peptide was measured.

Specifically, human erythrocyte was diluted in physiological saline (PBS, pH 7.4) to have concentration of 8%, and then subjected to a treatment with myxinidin, myxinidin 1, myxinidin 2, or myxinidin 3 peptide, each at concentration of 3.125, 6.25, 12.5, or 25.0 µM/well, followed by reaction for 1 hour at 37° C. After that, the amount of hemoglobin contained in a supernatant collected by centrifuge at 1,000×g was determined by measuring the absorbance at a wavelength of 414 nm. As a control group to be used as a reference for cell disruption level, the supernatant collected by a treatment with 1% Triton X-100 (Sigma, USA) and reaction for 1 hour at 37° C. was used to measure the absorbance. By setting the erythrocyte hemolytic activity of Triton X-100 at 100%, the hemolytic activity of the above peptides was calculated using the following mathematical equation 1.

Erythrocyte disrupting ability(hemolysis)(%)=(Absorbance $A$–Absorbance $B$)/(Absorbance $C$–Absorbance $B$)×100    [Mathematical equation 1]

(in the above equation, Absorbance A indicates the absorbance of a reaction solution treated with each peptide, in which the absorbance is measured at a wavelength of 414 nm; Absorbance B indicates the absorbance of a reaction solution treated with PBS, in which the absorbance is measured at a wavelength of 414 nm; and Absorbance C indicates the absorbance of a reaction solution treated with 1% Triton X-100, in which the absorbance is measured at a wavelength of 414 nm).

As a result, it was found that, when human erythrocyte is treated with 25 µM myxinidin as a mother peptide or myxinidin 1, myxinidin 2, and myxinidin 3 as a test peptide, myxinidin 2 and myxinidin 3 peptides induced the hemolytic activity of 2% or 12%. Accordingly, it was confirmed that the antimicrobial peptide of the present invention has low cytotoxicity for erythrocyte (Table 6).

TABLE 6

| | Erythrocyte disrupting ability % (concentration of each peptide, µM) | | | |
|---|---|---|---|---|
| Peptide | 25 | 12.5 | 6.25 | 3.125 |
| Myxinidin | 3 | 2 | 1 | 0 |
| Myxinidin 1 | 2 | 1 | 0 | 0 |
| Myxinidin 2 | 2 | 1 | 0 | 0 |
| Myxinidin 3 | 12 | 5 | 1 | 0 |

Example 6: Determination of Cytotoxicity in Normal Cell Line

To determine the cytotoxicity of the peptide produced by the method of Example 1 in normal cell line, toxicity was measured by using NHK cells (Normal Human Keratinocyte cells).

Specifically, NHK cells which have been cultured in Epilife medium with 60 µM calcium (Gibco, USA) containing 10% HKGS (Human Keratinocyte Growth Supplement) (Gibco, USA) were aliquoted in a 96-well plate to have $1 \times 10^4$ cells per well. After culturing them for 24 hours, the cells were subjected to a treatment with myxinidin, myxinidin 1, myxinidin 2, or myxinidin 3 peptide, each at concentration of 3.125, 6.25, 12.5, or 25.0 µM/well, followed by reaction for 24 hours in a 5% $CO_2$ incubator. After the culture, a reaction solution containing 5 mg/ml MTT (Thiazolyl Blue Tetrazolium Bromide) dissolved in physiological saline (PBS) was added in an amount of 20 µl to each well and allowed to react for 4 hours. After that, the supernatant was removed, and, by dissolving MTT crystals that are formed by adding 200 μl of DMSO, the absorbance at 560 nm was measured to determine the cell survival ability.

As a result, it was found that, when the cells are treated with myxinidin as a mother peptide or myxinidin 1, myxinidin 2, and myxinidin 3 within an active concentration range, 98% or higher cell survival ability of the NHK cells was shown at a concentration of 12.5 μM or less. Accordingly, it was confirmed that myxinidin 2 or myxinidin 3 peptide have almost no cytotoxicity (Table 7).

TABLE 7

| Peptide | Cell survival ability % (concentration of each peptide, μM) | | | |
|---|---|---|---|---|
|  | 25 | 12.5 | 6.25 | 3.125 |
| Myxinidin | 95 | 98 | 98 | 100 |
| Myxinidin 1 | 88 | 96 | 96 | 100 |
| Myxinidin 2 | 75 | 98 | 100 | 100 |
| Myxinidin 3 | 100 | 100 | 100 | 100 |

Example 7: Measurement of Circular Dichroism Spectrum

To determine whether or not an α-helical structure or a β-sheet structure as a secondary structure is induced by the peptide produced by the method of Example 1, measurement was carried out using circular dichroism.

Specifically, myxinidin, myxinidin 1, myxinidin 2, or myxinidin 3 peptide which have been synthesized in above Example 1 was added at a concentration of 50 μM to physiological saline (PBS, pH 7.4), PG, PE:PG, PC, PC:CH, PC:SM, or SM solution. After adding the mixture to a cell with 0.1 cm path length, the temperature was set at 25 D and a circular dichroism spectrum was measured by using Jasco 810 spectrophotometer.

Figure 1B:
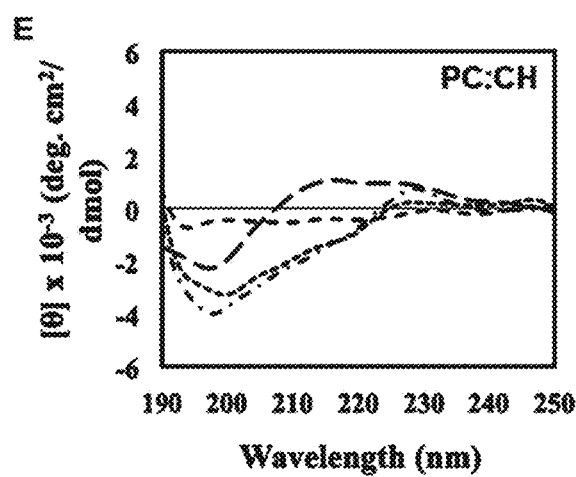
Figure 1B:
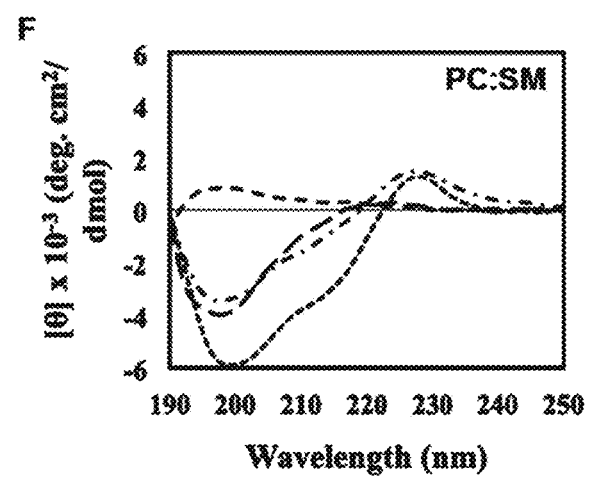
Figure 1B:
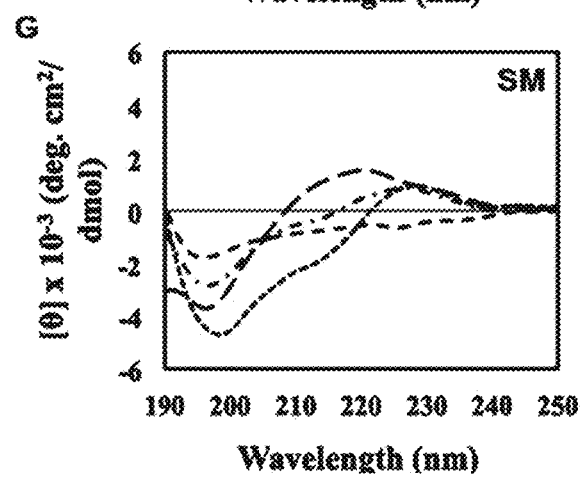

As a result, as it is shown in FIGS. 1A and 1B, no structure forming was seen when the peptide is added to physiological saline (PBS), but an α-helical structure or a β-sheet structure as a secondary structure is formed by myxinidin 2 and myxinidin 3 peptides are added to PG or PE:PG, although there is a difference in the level of structure forming. Based on those results, it was confirmed that the antimicrobial peptide of the present invention can form an α-helical structure or a β-sheet structure in PE or PE:PG, that are similar to a membrane of bacteria as microbes. It was also confirmed that no such structure is formed in an animal cell membrane like PC, PC:CH, PC:SM, and SM.

Example 8: Confocal Microscopy Analysis

To determine any activity of the peptide produced by the method of Example 1 exhibited on membrane of *Escherichia coli* and *Staphylococcus aureus*, myxinidin 2 or myxinidin 3, which are selected as a peptide having high antimicrobial activity without showing any cytotoxicity, was treated with PI (Propidium iodide) followed by confocal microscopy analysis.

Specifically, myxinidin 2 or myxinidin 3, which have been synthesized in the above Example 1, was treated with PI (Propidium Iodide) solution and *Escherichia coli* or *Staphylococcus aureus* followed by reaction for 10 minutes. After the reaction, only pure *Escherichia coli* were collected by centrifuge (4,000 rpm) followed by removal of supernatant. Then, by adding 50 μl of physiological saline (PBS), cell aggregate was removed. By using LSM510 confocal microscope, the working mechanism of the peptide on *Escherichia coli* and *Staphylococcus aureus* membrane was determined.

Figure 2:
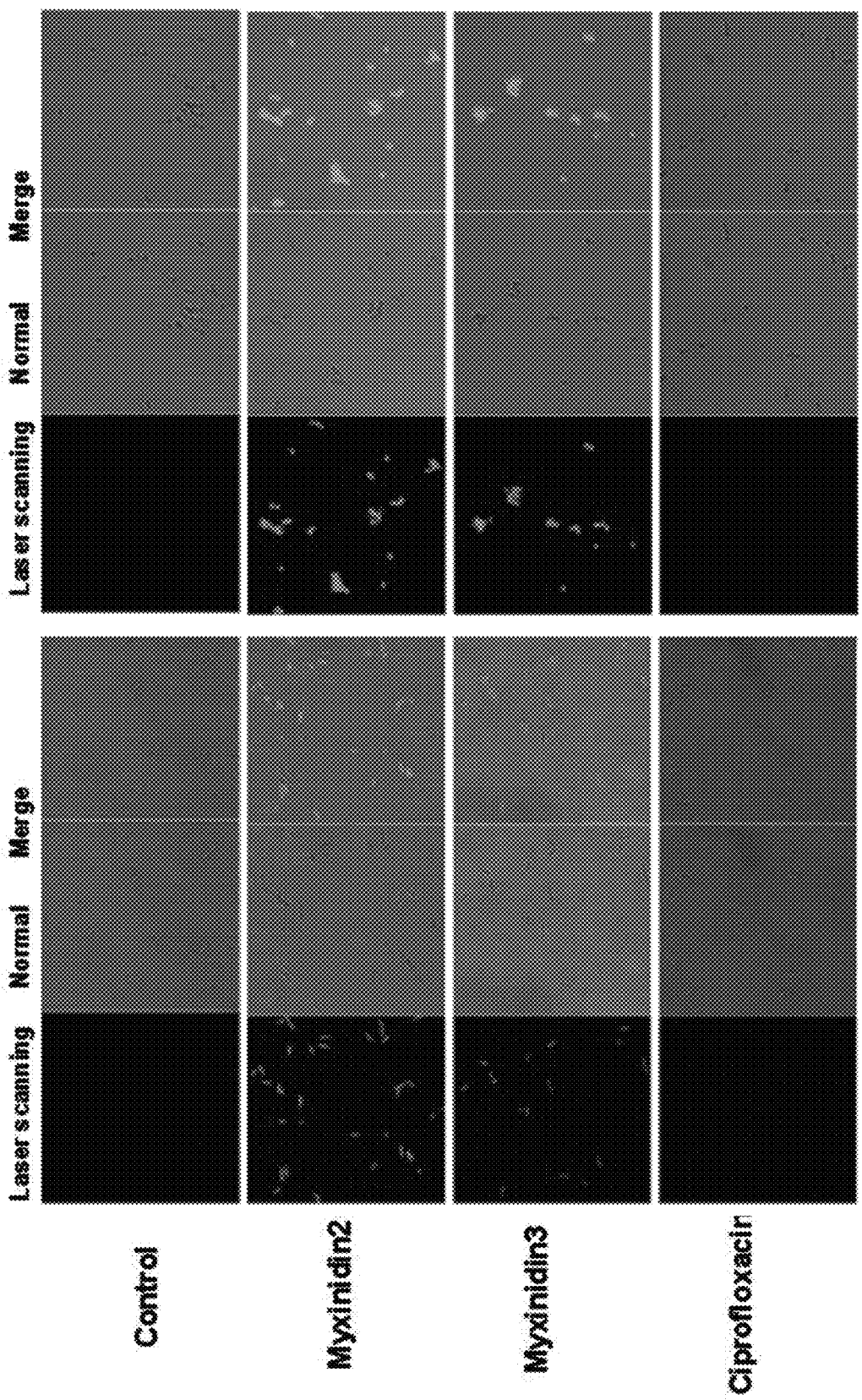
FIG. 2 shows the result of determining the working activity of the control group, peptides of myxinidin 2 and myxinidin 3, and ciprofloxacin on membrane of *Escherichia coli* (*E. coli*) and *Staphylococcus aureus* (*S. aureus*).

As a result, it was found that both myxinidin 2 and myxinidin 3 peptide work on the membrane of *Escherichia coli* and *Staphylococcus aureus* to show PI, as it is illustrated in FIG. 2.

Example 9: Determination of Effect of Antimicrobial Peptide on *Escherichia coli* and *Staphylococcus aureus*

To specifically determine the level of the antimicrobial activity exhibited by the synthetic peptide of the present invention, the *Escherichia coli* and *Staphylococcus aureus* membrane disrupting ability of myxinidin as a mother peptide or myxinidin 1, myxinidin 2, and myxinidin 3 as a synthetic peptide was measured by scanning electron microscopy (SEM).

Specifically, *Escherichia coli* were cultured in LB medium (1% bacto tryptone, 0.5% bacto yeast extract, and 1% sodium chloride) and *Staphylococcus aureus* were cultured in TSB medium, each to a mid-log phase, followed by dilution in physiological saline to have cell body concentration of $2 \times 10^7$ cells/ml. The diluted bacterial strain was treated with myxinidin synthesized in Example 1 or myxinidin 1 to myxinidin 3 peptides as a comparative group, each at concentration of MIC, and the reaction was allowed to occur for 30 minutes at 37° C. After that, 2.5% glutaraldehyde was added to the bacterial strain to fix the cells for 30 minutes at room temperature and for 12 hours at 40 followed by washing with buffer and re-fixing with $OsO_4$. Then, stepwise dehydration was carried out by using ethanol. After the dehydration, platinum coating was carried out and the observation was made by using low vacuum scanning electron microscopy.

Figure 3:
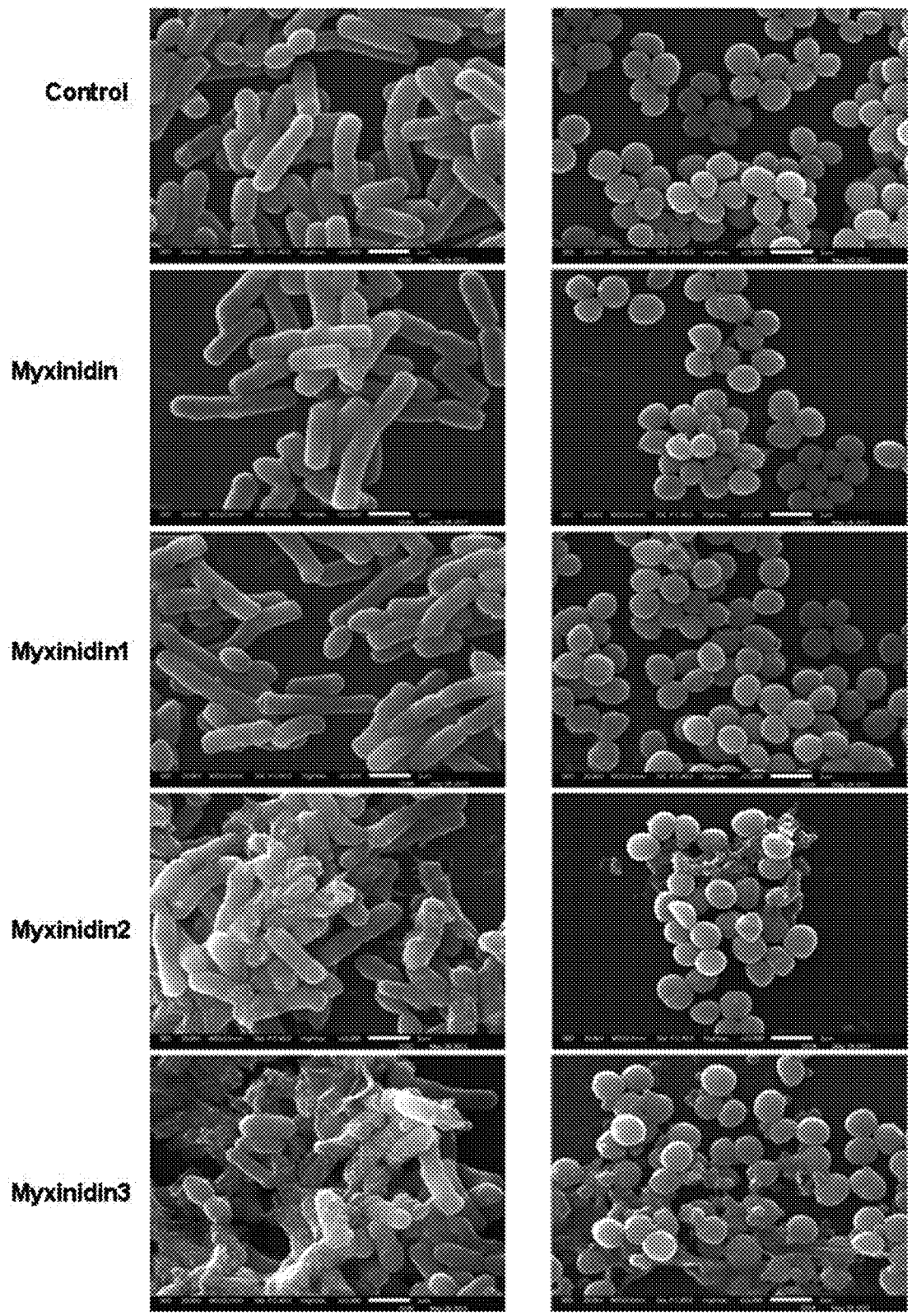
FIG. 3 shows the result of determining the activity of peptides of myxinidin, myxinidin 1, myxinidin 2, and myxinidin 3 for disrupting membrane of *E. coli* (left) and *S. aureus* (right).

As a result, it was found as it is illustrated in FIG. 3 that, when *Escherichia coli* membrane is treated with myxinidin to myxinidin 3, myxinidin 2 and myxinidin 3 peptides worked on the *Escherichia coli* membrane to yield membrane disruption, and thus showing an effective antimicrobial activity.

Example 10: Determination of Antimicrobial Activity Exhibited on Bacteria Having Tolerance to Antibiotics when Antimicrobial Peptide is Admixed with Gelatin which is Used as a Wound Moisturizing Agent To specifically determine the antimicrobial activity at the time of mixing the synthetic peptide of the present invention with gelatin, myxinidin 2 and myxinidin 3 synthetic peptides were admixed with 0.1% gelatin. Furthermore, to determine the antimicrobial activity, a minimum inhibitory concentration measurement and an anti-microbial disk diffusion susceptibility test as an agar diffusion method were carried out for *Acinetobacter baumannii, Pseudomonas aeruginosa,* and *Staphylococcus aureus.*

Specifically, cultured *Acinetobacter baumannii, Pseudomonas aeruginosa,* and *Staphylococcus aureus* were diluted to a concentration of $2 \times 10^5$ cells/ml, admixed with a solution in which 0.1% gelatin is mixed with 1% agarose, and cultured. To see the antimicrobial activity, the peptide was applied on a 6 mm round disk, in which the peptide was applied at various different concentrations, and the diffusion level was measured.

Figure 4A:
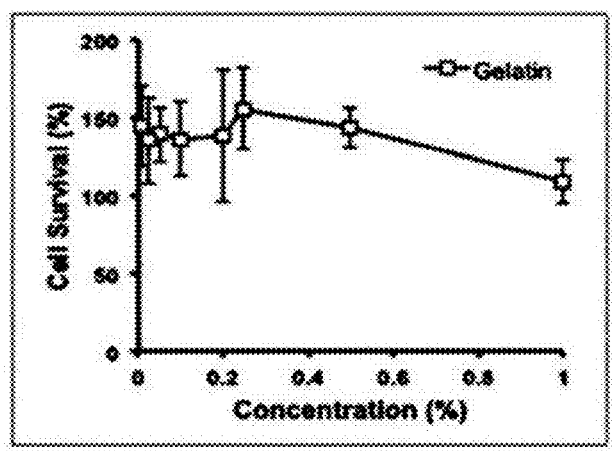
FIGS. 4A to 4C show the results of determining the antimicrobial activity when the peptides of the present invention are admixed with gelatin used as a wound moisturizing agent.
Figure 4B:
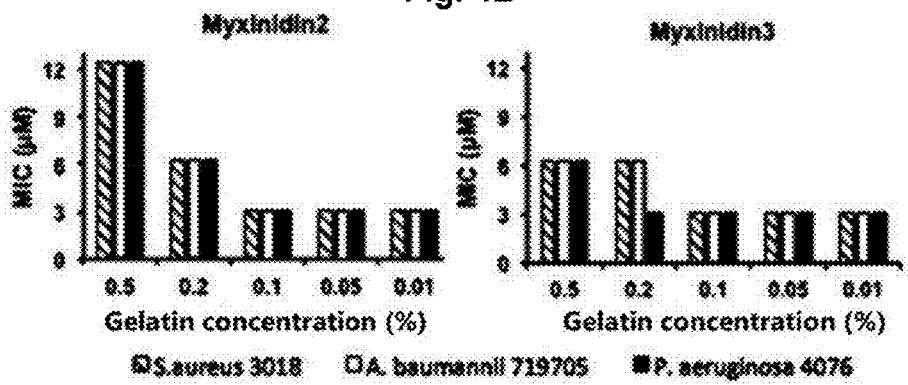
Figure 4C:
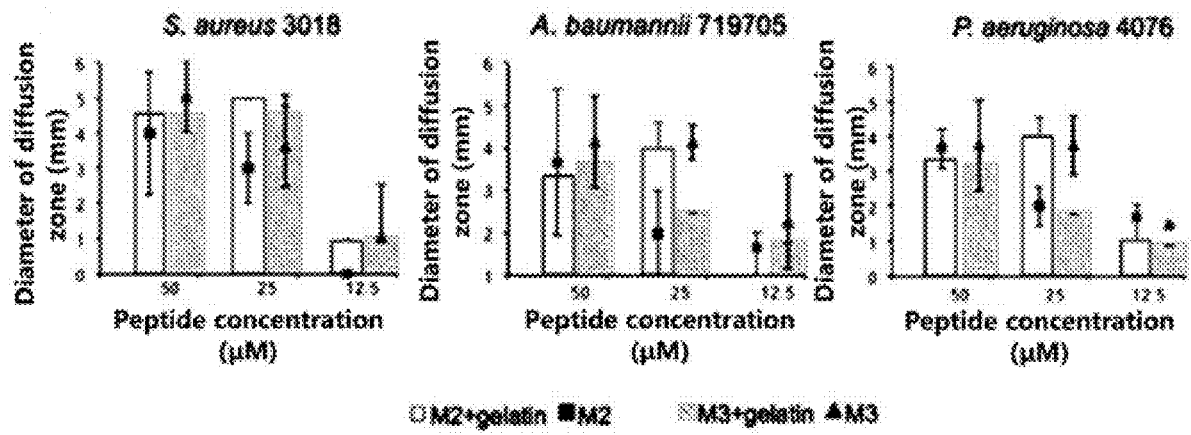

As a result, it was shown that antimicrobial peptide myxinidin 2 and myxinidin 3 mixed with gelatin exhibited the antimicrobial activity for *Staphylococcus aureus, Acinetobacter baumannii*, and *Pseudomonas aeruginosa*, which are bacteria having tolerance, while the peptides maintain the antimicrobial activity (see FIGS. 4A to 4C). Thus, it was found that gelatin used as a wound moisturizing agent can maintain the antimicrobial activity of an antimicrobial peptide even if it is used after being mixed with the antimicrobial peptide.

FIG. 4B is a graph to determine whether or not the peptide can maintain the normal antimicrobial activity as gelatin is a sticky material by nature, and to determine the use concentration of gelatin. From the figure, it was confirmed that, when gelatin concentration is 0.1%, the antimicrobial activity of the peptide was maintained at antimicrobial peptide MIC of 3.1 μM.

It was also found that, as a result of measuring the antimicrobial activity of the peptide with 0.1% gelatin concentration, a similar antimicrobial activity was maintained for myxinidin 2 and myxinidin 3 even when they are used with gelatin in *Staphylococcus aureus* 3018. In case of *Acinetobacter baumannii* 719705, the antimicrobial activity was maintained even when myxinidin 2 is used with gelatin, while myxinidin 3 exhibited a slightly higher antimicrobial activity when the treatment is made only with the peptide. In the latter case, the activity was still maintained even in the presence of gelatin. The activity observed from *Pseudomonas aeruginosa* 4076 was similar to *Acinetobacter baumannii* (see, FIG. 4C).

Furthermore, as a result of determining the presence or absence of toxicity at the time of treating skin keratinocyte cells with gelatin at different concentrations (i.e., 0% to 1%), no toxicity was shown and the cell proliferation was yielded instead, and thus it was able to confirm the cell survival rate of at least 100% (see, FIG. 4A).

Example 11: Determination of Proteins that are Expressed by Action of Antimicrobial Peptide in Skin Keratinocyte Cells Infected with Bacteria Having Tolerance to Antibiotics, and Signaling Pathway Thereof To specifically determine the proteins that are expressed by an action of the synthetic peptide in skin keratinocyte cells infected with *Acinetobacter baumannii, Pseudomonas aeruginosa*, or *Staphylococcus aureus*, analysis was made by using Western blot, and the signaling pathway of the expression was determined.

Specifically, skin keratinocyte cells were first cultured at concentration of $5 \times 10^5$ cells/ml and then infected with *Acinetobacter baumannii, Pseudomonas aeruginosa*, or *Staphylococcus aureus*. After that, the cells were treated with the peptide at a concentration that is 2 times higher than the minimum inhibitory concentration, and the protein was extracted. Then, 30 to 40 μg of the protein was electrophoresed on 10% or 12% SDS polyacrylamide gel followed by transfer on a PVDF membrane. Expression amount and phosphorylation of STAT3, SAPK/JNK, P38, and EGFR proteins were determined by Western blot analysis.

Figure 5:
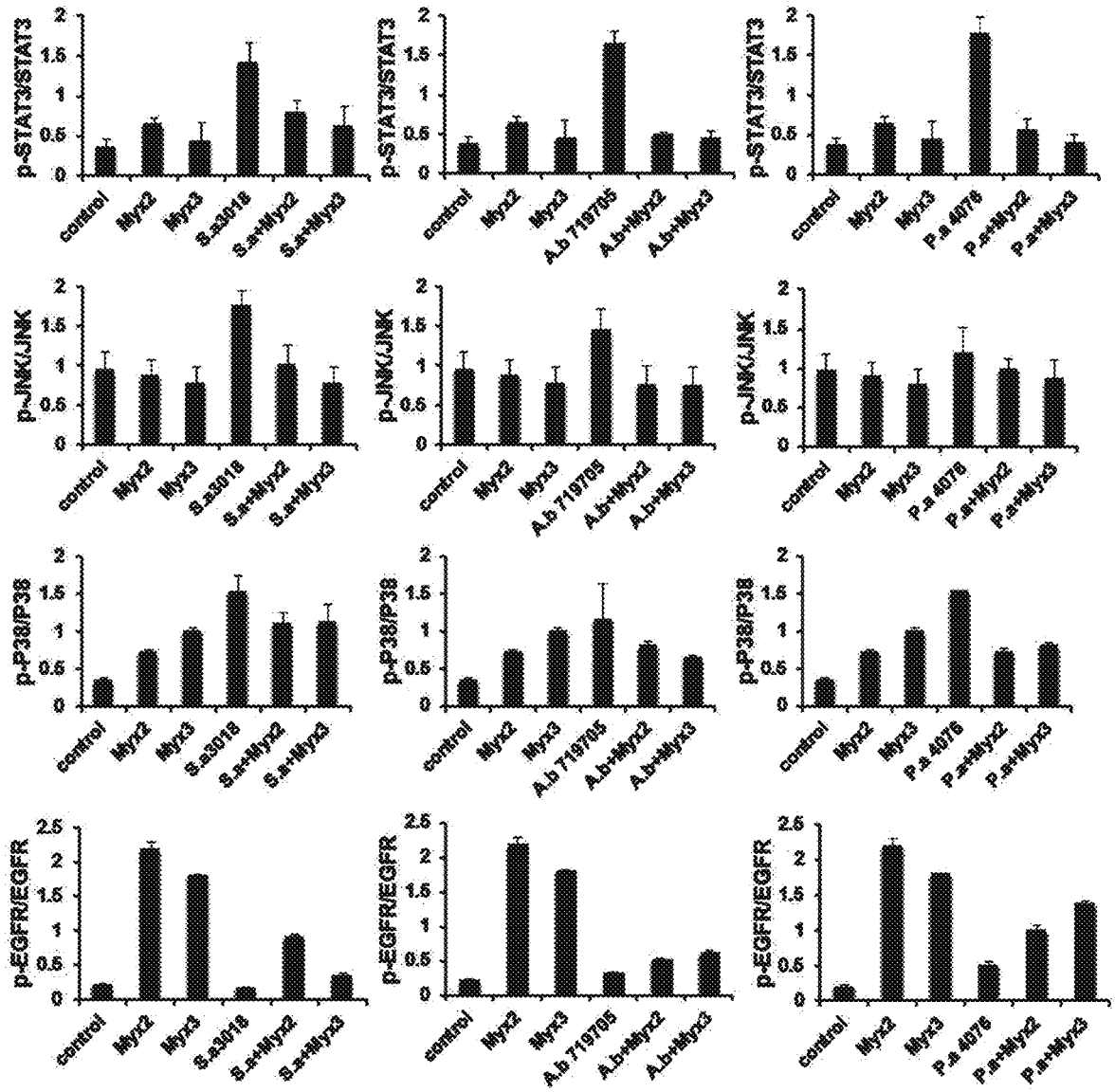
FIG. 5 shows the result of the Western blot analysis of phosphorylation and expression amount of STAT3, SAPK/JNK, P38, and EGFR when an antimicrobial peptide treatment is carried out for skin keratinocyte cells which have been infected with microbes with antibiotics resistance. In the figure, Myx2 represents myxinidin 2, Myx3 represents myxinidin 3, S.a represents *Staphylococcus aureus*, A.b represents *Acinetobacter baumannii*, and P.a represents *Pseudomonas aeruginosa*.

STAT is a transcription factor for expressing cytokine and growth factor. As being involved with cell growth and death, in case of having inflammation, STAT is phosphorylated by proinflammatory cytokine like IL-6 and TNF-α to exhibit the activity. Accordingly, it was confirmed that infection with bacteria having tolerance to antibiotics yields inflammation to show increased STAT3 phosphorylation while the reduced phosphorylation is shown after a treatment with the peptide (see, FIG. 5). Among MAP kinases present in downstream signaling pathway, SAPK/JNK and P38 contribute to an inflammatory response and regulate cellular function such as cell growth, differentiation, or survival. In the infected cells, increased phosphorylation of SAPK/JNK and P38 was shown, but reduced phosphorylation of SAPK/JNK and P38 was shown after a treatment with the peptide (see, FIG. 5). Epidermal growth factor receptor (EFGR) as one member of cell surface receptors binds to an epidermal growth factor and a growth factor-α, leading to MAP kinase downstream signal transduction to get involved with DNA synthesis, cell migration, adhesion, and proliferation. According to a treatment with the antimicrobial peptide, phosphorylation of an epidermal growth factor receptor is increased in infected cells, yielding cell growth (see, FIG. 5).

Example 12: Determination of Anti-Inflammatory Effect of Antimicrobial Peptide on Skin Keratinocyte Cells Infected with Bacteria Having Tolerance to Antibiotics To specifically determine the anti-inflammatory effect of the synthetic peptide of the present invention, infection with *Acinetobacter baumannii, Pseudomonas aeruginosa*, or *Staphylococcus aureus* and a treatment with myxinidin 2 and myxinidin 3 synthetic peptides were carried out, and interleukin-6 (IL-6) and interleukin-8 (IL-8), which are a cytokine and a chemokine, and tumor necrosis factor alpha (TNF-α) were analyzed by enzyme-linked immunosorbent assay.

Specifically, interleukin-6, interleukin-8, and tumor necrosis factor-α were analyzed by a human immune assay kit. Human skin keratinocyte cells were infected with *Staphylococcus aureus, Acinetobacter baumannii*, or *Pseudomonas aeruginosa*, which are the bacterial strain having tolerance to antibiotics, followed by a treatment with the peptide at a concentration that is 2 times higher than the minimum inhibitory concentration to have a reaction. After that, only the supernatant was collected and subjected to an enzyme-linked immunosorbent assay.

Figure 6:
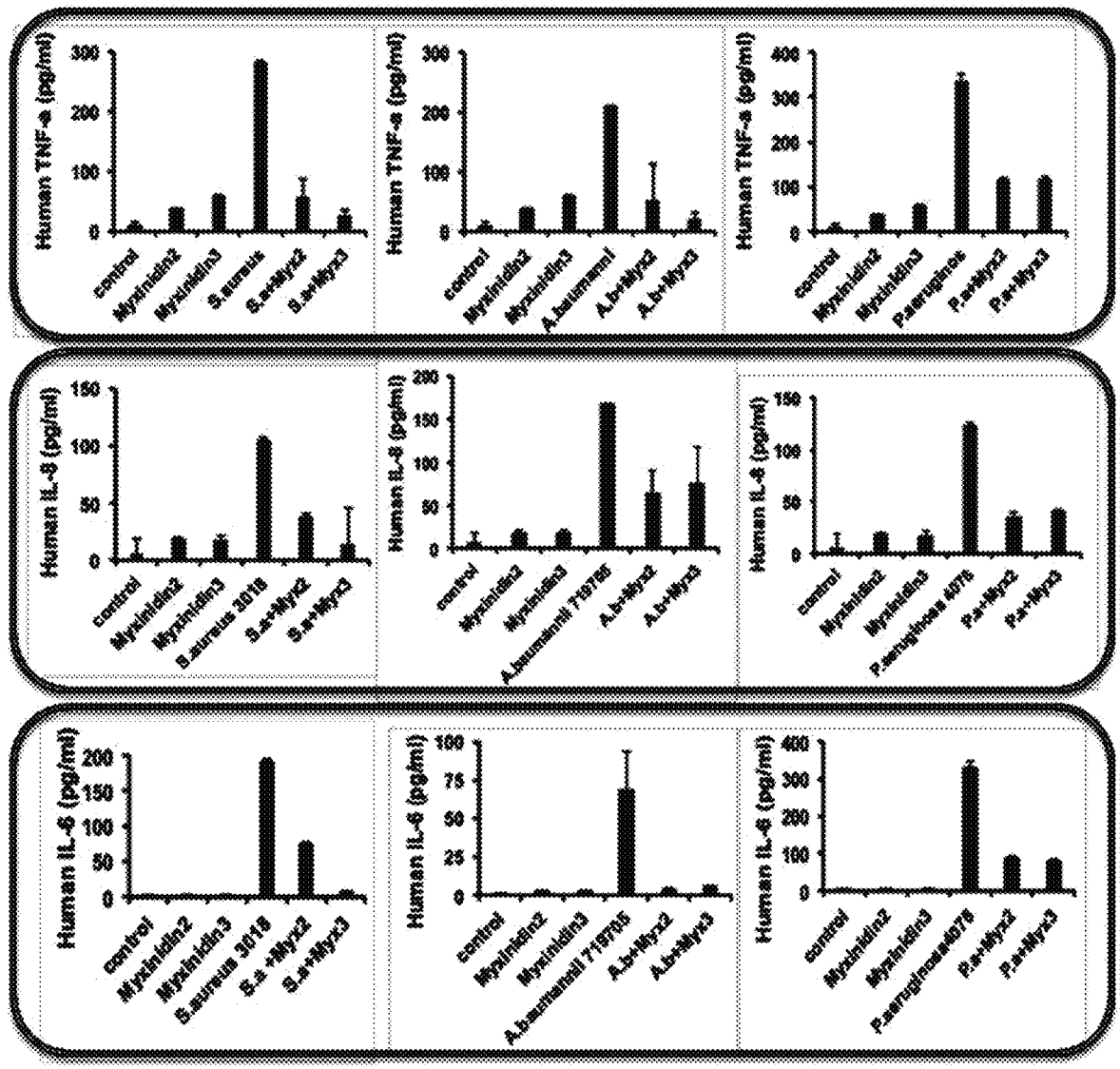
FIG. 6 shows the result of ELISA analysis of the expression amount of TNF-α, IL-6, and IL-8 to determine the anti-inflammatory effect that is exhibited by a treatment with the antimicrobial peptide in skin keratinocyte cells which have been infected with antibiotics-resistant bacteria. Myx2 represents myxinidin 2, Myx3 represents myxinidin 3, S.a represents *Staphylococcus aureus*, A.b represents *Acinetobacter baumannii*, and P.a represents *Pseudomonas aeruginosa*.

As a result, interleukin-6 and TNF-α as a cytokine secreted during inflammation, and interleukin-8 as a chemokine secreted during inflammation have rapidly increased when the cells were infected with *Staphylococcus aureus, Acinetobacter baumannii*, or *Pseudomonas aeruginosa*, which are the bacterial strain having tolerance to antibiotics. However, according to a treatment with myxinidin 2 or myxinidin 3 as an antimicrobial peptide, expression of the cytokine and chemokine that are secreted during an inflammatory response has decreased (see, FIG. 6).

Example 13: Determination of Wound Healing Effect of Antimicrobial Peptide Based on Migration of Skin Keratinocyte Cells Infected with Bacteria Having Tolerance to Antibiotics To determine the wound healing effect of the peptide of the present invention by activating migration of skin keratinocyte cells infected with *Acinetobacter baumannii, Pseudomonas aeruginosa*, or *Staphylococcus aureus*, which are the bacterial strain having tolerance to antibiotics, the adhered cells were damaged to have an infection followed by a treatment with myxinidin 2 or myxinidin 3. The resulting cells were then observed under a microscope.

Specifically, human skin keratinocyte cells were cultured at $1\times10^6$ cells/ml, and then scraped off using a tip. Then, the cells were infected with *Staphylococcus aureus, Acinetobacter baumannii*, or *Pseudomonas aeruginosa*, which are the bacterial strain having tolerance to antibiotics, followed by a treatment with the peptide at a concentration that is 2 times higher than the minimum inhibitory concentration. Cell migration was then observed under a microscope.

Figure 7A:
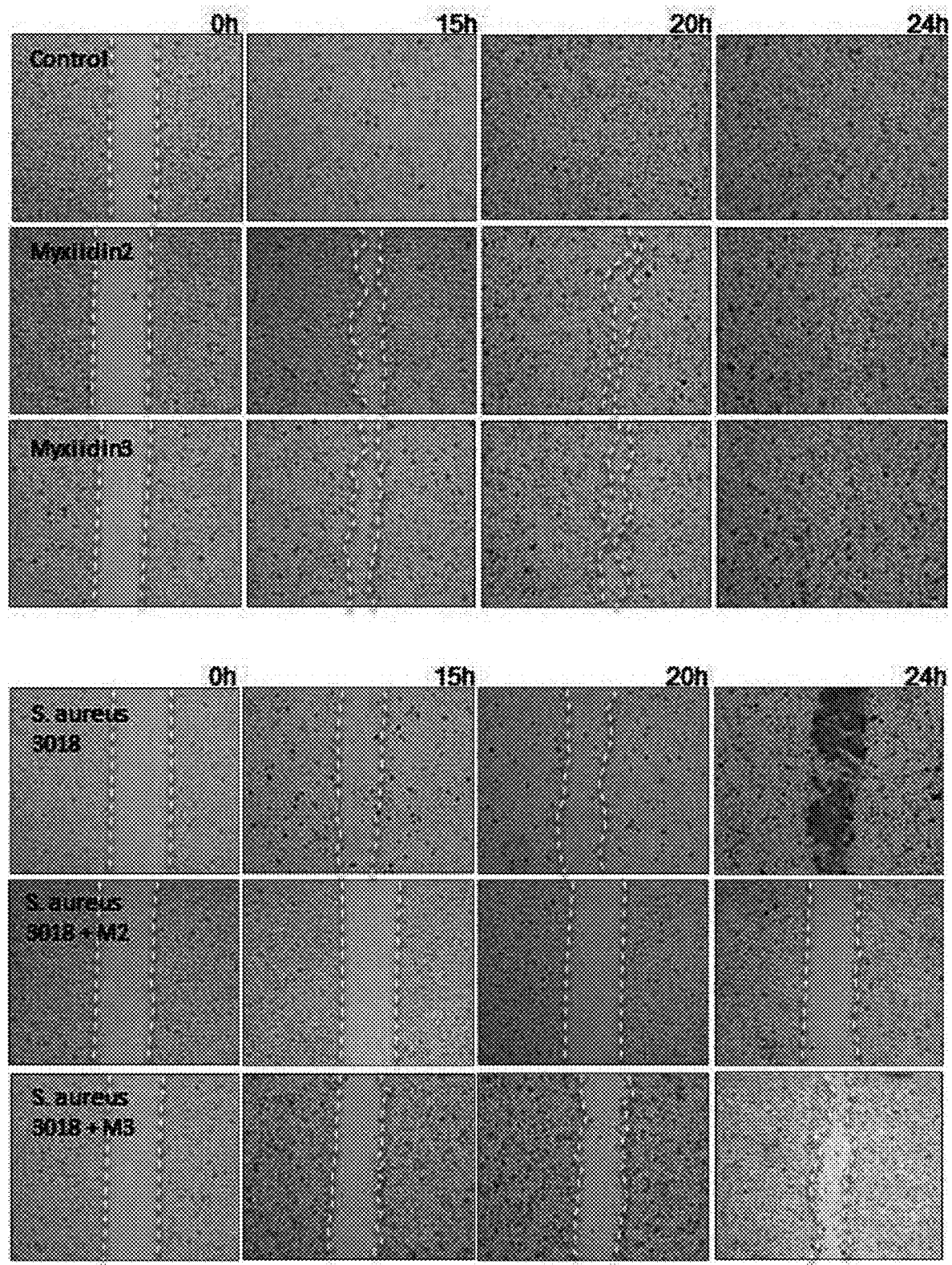
FIGS. 7A and 7B show the results of determining the wound healing effect exhibited by the antimicrobial peptide in skin keratinocyte cells which have been infected with antibiotics-resistant bacteria. Myx2 represents myxinidin 2 and Myx3 represents myxinidin 3.
Figure 7B:
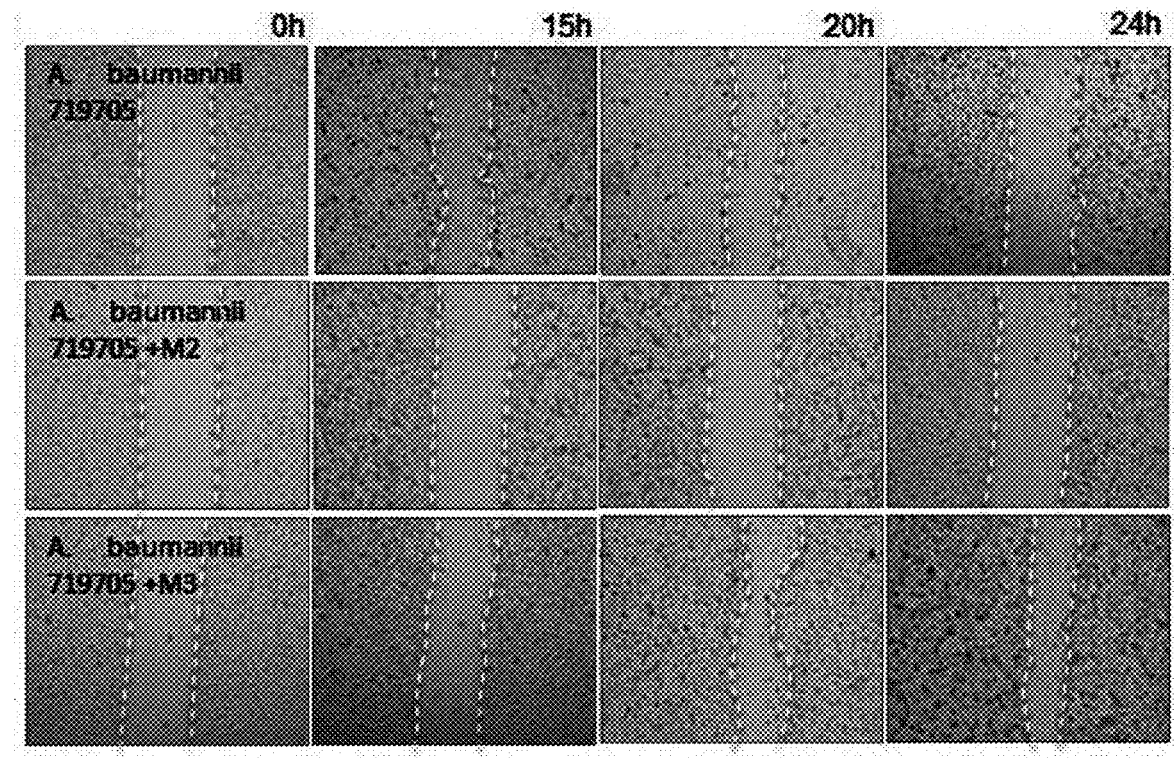
Figure 7B:
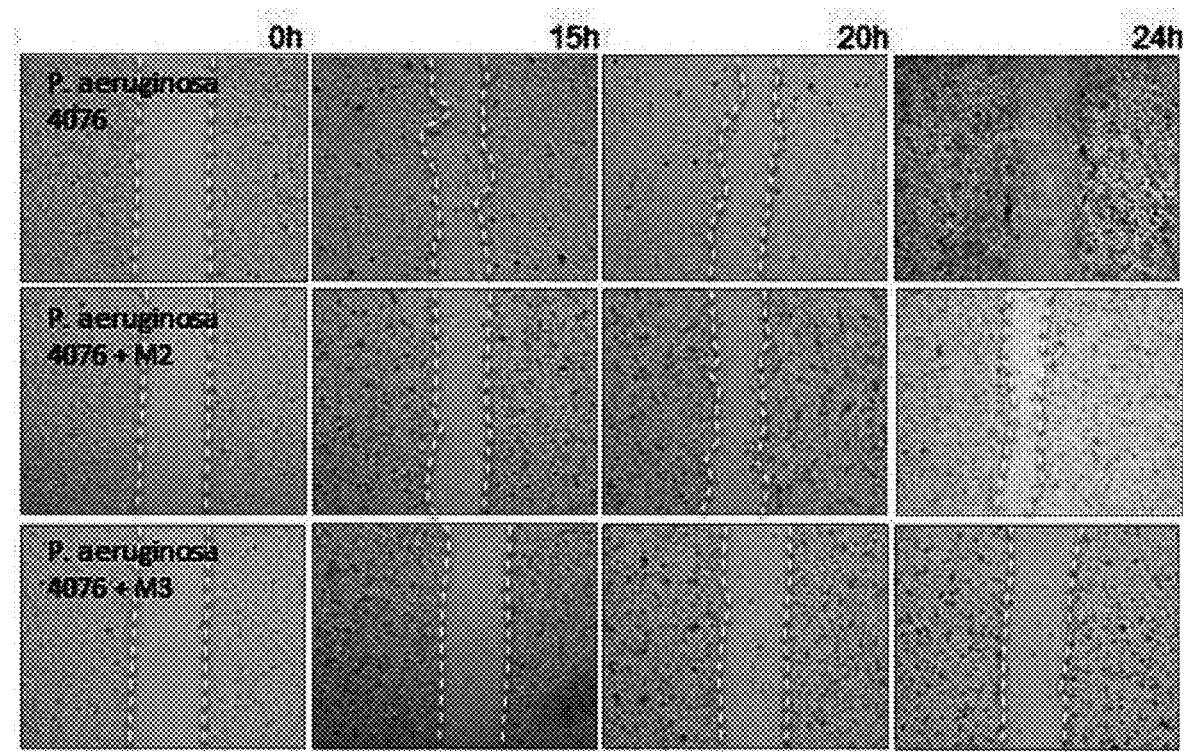

As a result, the infected skin keratinocyte cells showed significantly less migration over time, and it was confirmed that the cell death was yielded without filling a scraped region (see FIGS. 7A and 7B). On the other hand, the infected skin keratinocyte cells that are treated with an antimicrobial peptide showed increased cell migration from Hour 20, and at Hour 24, rapid cell migration was observed (see FIGS. 7A and 7B). In case of infection with *Staphylococcus aureus*, more rapid regeneration was obtained according to a treatment with myxinidin 3. Proliferation with no cell death was also achieved with myxinidin 2 although the proliferation rate was slow. Also in case of infection with *Acinetobacter baumannii*, fast regeneration rate was achieved with a treatment with myxinidin 3, and proliferation with no cell death was still achieved with myxinidin 2. In case of infection with *Pseudomonas aeruginosa*, fast regeneration rate was achieved with a treatment with myxinidin 2 and proliferation with no cell death was still achieved with myxinidin 3. Accordingly, it was found that the antimicrobial effect and cell migration are enhanced by a treatment of an infected wound with the antimicrobial peptide, showing a rapid progress of wound healing.

Example 14: Determination of Anti-Inflammatory Effect and Wound Healing of Antimicrobial Peptide on Skin Wound of Mouse which is Infected with Bacteria Having Tolerance to Antibiotics Healing process of skin wound of a mouse induced by the synthetic peptide of the present invention, in which the mouse has been infected with *Acinetobacter baumannii, Pseudomonas aeruginosa*, or *Staphylococcus aureus* as the bacterial strain having tolerance to antibiotics, was observed during different time periods. The animal tissue was stained by hematoxylin and eosin (H & E) staining to examine the skin tissue having inflammation.

Specifically, a wound was created in a 6 week to 7 week old BALB/c female mouse using 5 mm biopsy punch. Then, the mouse was infected with *Staphylococcus aureus, Acinetobacter baumannii*, or *Pseudomonas aeruginosa*, which are the bacterial strain having tolerance to antibiotics, followed by administration of the peptide at a concentration that is 2 times higher than the minimum inhibitory concentration. Wound size and healing process were observed for 2 weeks, and on Day 3 and Day 7, the skin tissue with a size of 2 cm×2 cm was collected and subjected to hematoxylin and eosin staining to determine the inflammation level of skin tissue.

Figure 8A:
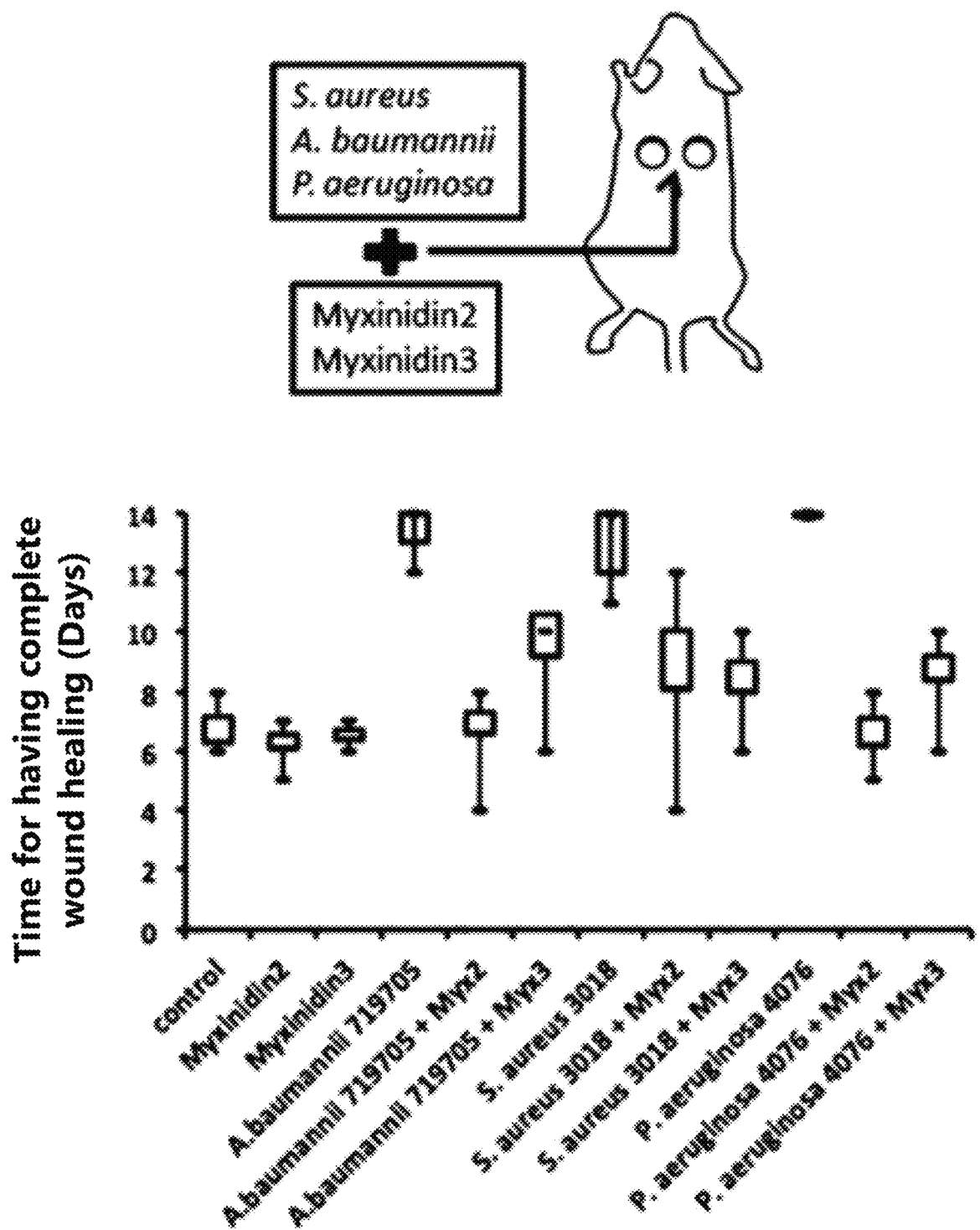
FIGS. 8A to 8C show the results of determining the wound healing effect exhibited by the antimicrobial peptide in mouse skin which has been infected with antibiotics-resistant bacteria, in which the wound healing effect is shown in terms of wound size reduction rate at different time points.
Figure 8B:
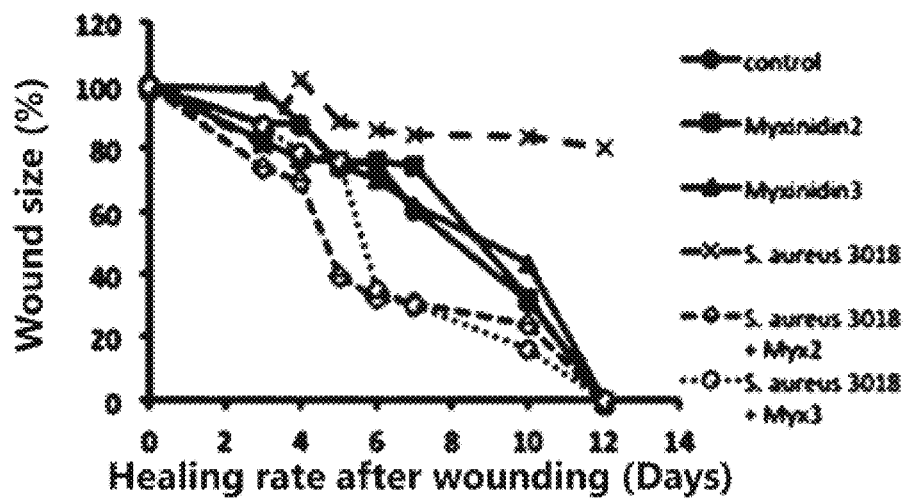
Figure 8B:
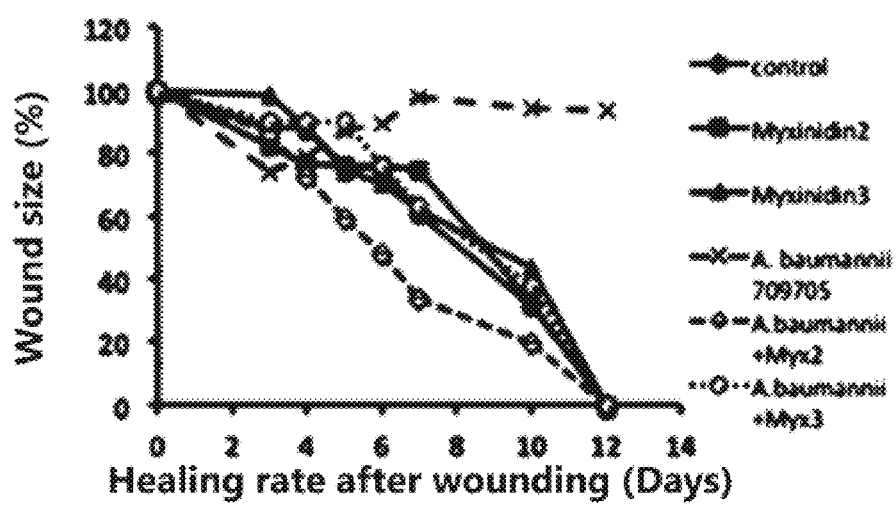
Figure 8B:
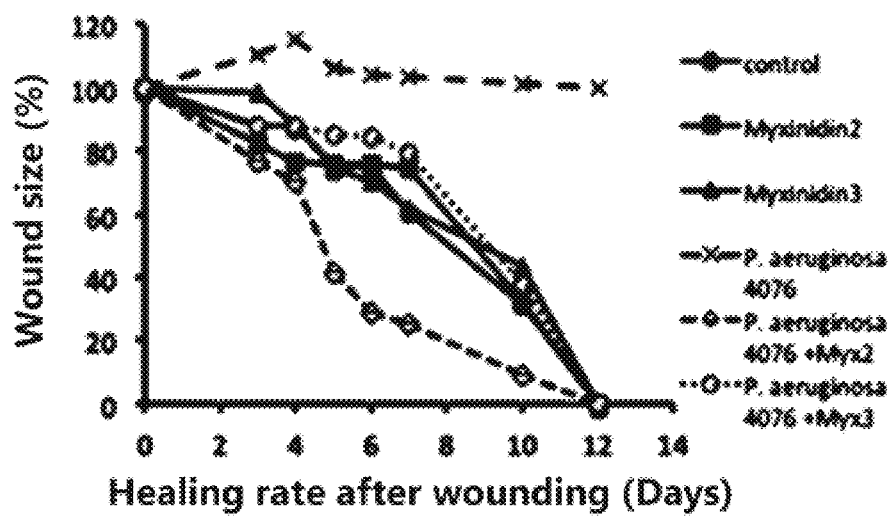
Figure 8C:
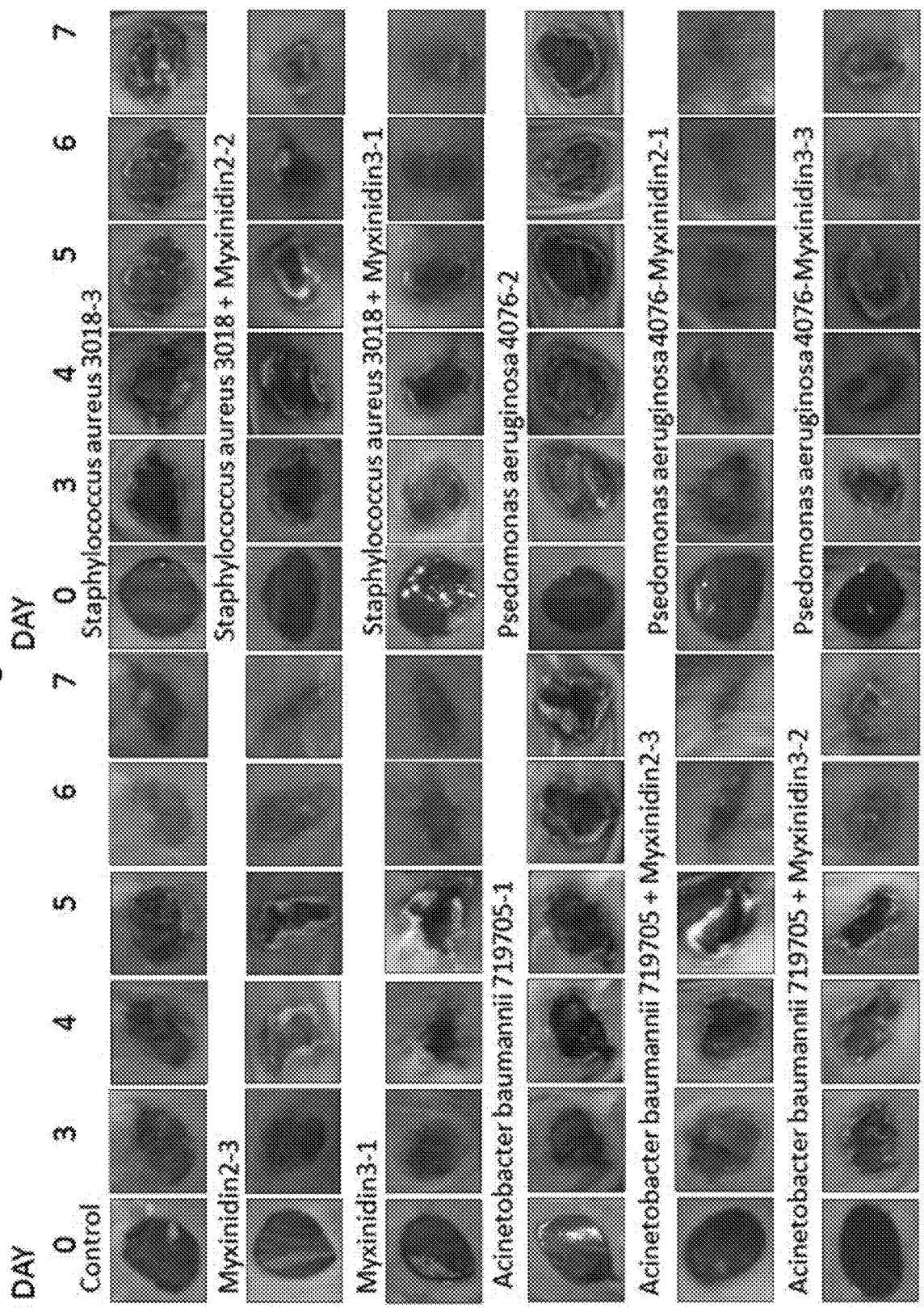

As a result, it was shown that the skin tissue of a mouse which has been infected with the bacteria having tolerance exhibited more aggravated inflammation without any wound healing, and exudate was secreted from the wound (see FIGS. 8A to 8C). On the other hand, the wound of a mouse administered with myxinidin 2 or myxinidin 3 as an antimicrobial peptide showed epidermalization and wound maturation. Thus, it was recognized that a treatment of infected wound with the antimicrobial peptide has an anti-inflammatory effect to yield wound healing with higher wound healing rate.

Figure 9:
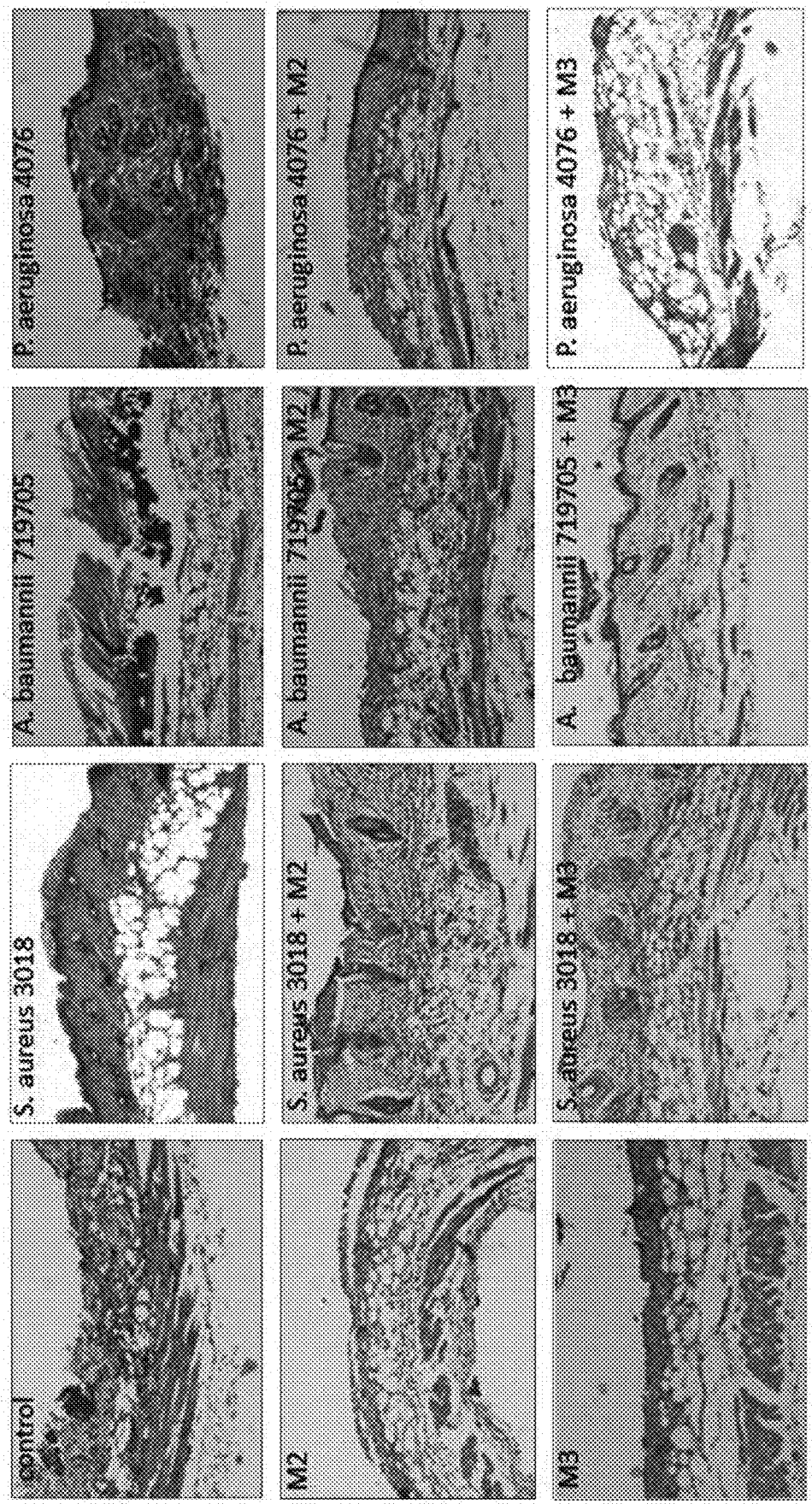
FIG. 9 shows the result of histopathological observation of the wound healing effect exhibited by the antimicrobial peptide in mouse skin which has been infected with antibiotics-resistant bacteria. Myx2 represents myxinidin 2 and Myx3 represents myxinidin 3.

As shown in FIG. 9, as a result of determining the inflammation level of the skin tissue on Day 7 by hematoxylin and eosin staining, it was confirmed that the skin inflammation is suppressed according to a treatment with the antimicrobial peptide.

Hereinbelow, preparation examples for producing the composition of the present invention are exemplified.

<Preparation Example 1> Production of Pharmaceutical Preparation

<1-1> Production of Powder Preparation

| | |
|---|---|
| Peptide of the present invention | 20 mg |
| Lactose | 20 mg |

After mixing the above components, a powder preparation was produced by filling them in a sealed pack.

<1-2> Production of Tablet

| | |
|---|---|
| Peptide of the present invention | 10 mg |
| Corn starch | 100 mg |
| Lactose | 100 mg |
| Magnesium stearate | 2 mg |

After mixing the above components, a tablet was produced according to tableting by a common method for producing a tablet.

<1-3> Production of Capsule Preparation

| | |
|---|---|
| Peptide of the present invention | 10 mg |
| Crystalline cellulose | 3 mg |
| Lactose | 14.8 mg |
| Magnesium stearate | 0.2 mg |

After mixing the above components, a capsule preparation was produced according to filling them in a gelatin capsule by a common method for producing a capsule preparation.

<1-4> Production of Liquid Preparation

| | |
|---|---|
| Peptide of the present invention | 20 mg |
| High fructose corn syrup | 10 g |
| Mannitol | 5 g |
| Purified water | suitable amount |

According to a common method for producing a liquid preparation, each component was added to purified water for dissolution. After adding a suitable amount of lemon flavor, the above components were admixed with one another followed by addition of purified water to adjust the entire volume to 100 ml. The mixture was then filled in a brown bottle followed by sterilization to produce a liquid preparation.

<1-5> Production of Injection Solution

| | |
|---|---|
| Peptide of the present invention | 10 μg/ml |
| Dil. hydrochloric acid BP | till to have pH 7.6 |
| Sodium chloride BP for injection | 1 ml at maximum |

In sodium chloride BP for injection with suitable volume, the peptide of the present invention was dissolved. pH of the resulting solution was adjusted to pH 7.6 by using dil. hydrochloric acid BP, and the volume was adjusted by using sodium chloride BP for injection followed by thorough mixing. The resulting solution was filled in a 5 ml Type I ampoule made of transparent glass. By melting the glass, the ampoule was sealed while having air in the top. Then, according to autoclave for 15 minutes or longer at 120☐, sterilization was carried out to produce an injection solution.

<Preparation Example 2> Production of Cosmetics

<2-1> Softening Cosmetic Water (Skin Lotion)

To produce a softening cosmetic water containing the peptide of the present invention, blending can be carried out as described in the following Table 8 and production can be made according to a common production method in the cosmetic field.

TABLE 8

| Component | Content (% by weight) |
| --- | --- |
| Peptide of the present invention | 0.1 to 30 |
| 1,3-Butylene glycol | 3.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-2> Nutritive Cosmetic Water (Lotion)

To produce an antimicrobial nutritive cosmetic water containing the peptide of the present invention, blending can be carried out as described in the following Table 9 and production can be made according to a common production method in the cosmetic field.

TABLE 9

| Component | Content (% by weight) |
| --- | --- |
| Peptide of the present invention | 0.1 to 30 |
| Squalane | 10.0 |
| Monooleic acid polyoxyethylene sorbitan | 2.0 |
| Lignum vitae oil | 0.1 to 30 |
| 1,3-Butylene glycol | 8.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-3> Essence

To produce an antimicrobial essence containing the peptide of the present invention, blending can be carried out as described in the following Table 10 and production can be made according to a common production method in the cosmetic field.

TABLE 10

| Component | Content (% by weight) |
| --- | --- |
| Peptide of the present invention | 0.1 to 30 |
| Sitosterol | 1.7 |
| Polyglyceryl 2-oleate | 1.5 |
| Ceramide | 0.7 |
| Ceteareth-4 | 1.2 |
| Cholesterol | 1.5 |
| Dicetyl phosphate | 0.4 |
| Conc. glycerin | 5.0 |
| Carboxyvinyl polymer | 0.2 |
| Xanthan gum | 0.2 |
| Preservative | trace amount |
| Fragrance | trace amount |
| Purified water | To 100 |

<2-4> Facial Cleanser (Cleansing Foam)

To produce an antimicrobial facial cleanser (cleansing foam) containing the peptide of the present invention, blending can be carried out as described in the following Table 11 and production can be made according to a common production method in the cosmetic field.

TABLE 11

| Component | Content (% by weight) |
| --- | --- |
| Peptide of the present invention | 0.1 to 30 |
| Sodium N-acylglutamate | 20.0 |
| Glycerin | 10.0 |
| PEG-400 | 15.0 |
| Propylene glycol | 10.0 |
| POE (15) oleyl alcohol ether | 3.0 |
| Laurin derivatives | 2.0 |
| Methyl paraben | 0.2 |
| EDTA-4Na | 0.03 |
| Fragrance | 0.2 |
| Purified water | To 100 |

<2-5> Nutritive Cream

To produce an antimicrobial nutritive cream containing the peptide of the present invention, as described in the following Table 12, production can be made according to a common production method in the cosmetic field.

TABLE 12

| Component | Content (% by weight) |
| --- | --- |
| Peptide of the present invention | 0.1 to 30 |
| Vaseline | 7.0 |
| Fluid paraffin | 10.0 |
| Bees wax | 2.0 |
| Polysorbate 60 | 2.5 |
| Sorbitan sesquioleate | 1.5 |
| Squalane | 3.0 |
| Propylene glycol | 6.0 |
| Glycerin | 4.0 |
| Triethanolamine | 0.5 |
| Xanthan gum | 0.5 |
| Tocopheryl acetate | 0.1 |
| Fragrance, preservative | trace amount |
| Purified water | To 100 |

<2-6> Massage Cream

To produce an antimicrobial massage cream containing the peptide of the present invention, as described in the following Table 13, production can be made according to a common production method in the cosmetic field.

TABLE 13

| Component | Content (% by weight) |
| --- | --- |
| Peptide of the present invention | 0.1 to 30 |
| Propylene glycol | 6.0 |
| Glycerin | 4.0 |
| Triethanolamine | 0.5 |
| Bees wax | 2.0 |
| Tocopheryl acetate | 0.1 |
| Polysorbate 60 | 3.0 |
| Sorbitan sesquioleate | 2.5 |
| Cetaryl alcohol | 2.0 |
| Fluid paraffin | 30.0 |
| Xanthan gum | 0.5 |
| Fragrance, preservative | trace amount |
| Purified water | To 100 |

<2-7> Pack

To produce an antimicrobial pack containing the peptide of the present invention, as described in the following Table 14, production can be made according to a common production method in the cosmetic field.

TABLE 14

| Component | Content (% by weight) |
| --- | --- |
| Peptide of the present invention | 0.1 to 30 |
| Propylene glycol | 2.0 |
| Glycerin | 4.0 |
| Polyvinyl alcohol | 10.0 |
| Ethanol | 7.0 |
| PEG-40 (Hydrogenated castor oil) | 0.8 |
| Triethanolamine | 0.3 |
| Fragrance, preservative | trace amount |
| Purified water | To 100 |

The present invention is not limited to Examples and Preparation examples that are described above and various modifications and changes can be made by a person skilled in the art. Also, an application can be made to cosmetics of various usages including color cosmetics. Furthermore, depending on the effect, use can be made for a pharmaceutical preparation which can be applied to human body by thin coating, i.e., ointment, and it is included in the spirit and scope of the present invention that is defined by the attached claims.

REFERENCE TO SEQUENCE LISTING

Pursuant to 37 C.F.R. § 1.821(c) or (e), an ASCII text file containing an electronic version of the Sequence Listing has been submitted concomitant with this application via EFS-Web, the contents of which are hereby incorporated by reference.

What is claimed is:

1. An antimicrobial peptide having the amino acid sequence of SEQ ID NO: 1,
wherein i) the $1^{st}$ and the $3^{rd}$ amino acids are substituted with lysine (K) or arginine (R), ii) the $7^{th}$ and the $10^{th}$ amino acids are optionally substituted with arginine (R), and iii) the $4^{th}$, the $9^{th}$, and the $11^{th}$ amino acids are substituted with tryptophan (W).

2. The antimicrobial peptide according to claim 1, wherein the antimicrobial peptide consists of the amino acid sequence of SEQ ID NO: 3 or SEQ ID NO: 4.

3. The antimicrobial peptide according to claim 1, wherein the antimicrobial peptide has an antimicrobial activity against Gram-negative bacteria, Gram-positive bacteria, or antibiotics-resistant bacteria.

4. The antimicrobial peptide according to claim 3, wherein the Gram-negative bacteria are at least one selected from a group consisting of *Escherichia coli, Pseudomonas aeruginosa, Salmonella typhimurium,* and *Acinetobacter baumannii.*

5. The antimicrobial peptide according to claim 3, wherein the Gram-positive bacteria are *Staphylococcus aureus* or *Listeria monocytogenes.*

6. The antimicrobial peptide according to claim 3, wherein the antibiotics-resistant bacteria are at least one selected from a group consisting of *Escherichia coli, Pseudomonas aeruginosa, Salmonella typhimurium, Staphylococcus aureus,* and *Acinetobacter baumannii* which have antibiotics resistance.

7. The antimicrobial peptide according to claim 1, wherein the antimicrobial peptide has low cytotoxicity for cells originating from human.

8. The antimicrobial peptide according to claim 1, wherein the antimicrobial peptide exhibits the antimicrobial activity even when it is admixed with gelatin used as a moisturizing agent.

9. A method for treating a microorganism or inflammation in a subject, the method comprising administering or applying an effective amount of a composition comprising the antimicrobial peptide of claim 1 to a subject in need thereof.

10. The method of claim 9, wherein the antimicrobial peptide has the amino acid sequence of SEQ ID NO: 3 or SEQ ID NO: 4.

11. The method of claim 9, wherein the microorganism is Gram-negative bacteria, Gram-positive bacteria, or antibiotics-resistant bacteria.

12. The method of claim 11, wherein the Gram-negative bacteria are at least one selected from a group consisting of *Escherichia coli, Pseudomonas aeruginosa, Salmonella typhimurium,* and *Acinetobacter baumannii.*

13. The method of claim 11, wherein the Gram-positive bacteria are *Staphylococcus aureus* or *Listeria monocytogenes.*

14. The method of claim 11, wherein the antibiotics-resistant bacteria are at least one selected from a group consisting of *Escherichia coli, Pseudomonas aeruginosa, Salmonella typhimurium, Staphylococcus aureus,* and *Acinetobacter baumannii* which have antibiotics resistance.

15. The method of claim 9, wherein the composition further comprises an antibiotics, an antibiotic cosmetic, an antibiotic food additive, an antibiotic animal feed additive, an antibiotic biopesticide, or an antibiotic quasi-drug.

16. The method of claim 9, wherein the method is for treating inflammation and comprises applying the composition to the subject.

17. The method of claim 9, wherein the composition further comprises an anti-inflammatory skin preparation for external use or a wound-healing skin preparation for external use.

\* \* \* \* \*